US009090942B2

(12) United States Patent
Inazawa et al.

(10) Patent No.: US 9,090,942 B2
(45) Date of Patent: Jul. 28, 2015

(54) METHOD FOR DETECTING ESOPHAGEAL CARCINOMA AND AGENT FOR SUPPRESSING ESOPHAGEAL CARCINOMA

(75) Inventors: Johji Inazawa, Tokyo (JP); Issei Imoto, Tokyo (JP); Shuhei Komatsu, Tokyo (JP); Ken-ichi Kozaki, Tokyo (JP); Hitoshi Tsuda, Tokyo (JP)

(73) Assignees: FUJIFILM Corporation, Tokyo (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 1486 days.

(21) Appl. No.: 12/730,919

(22) Filed: Mar. 24, 2010

(65) Prior Publication Data

US 2014/0018248 A1    Jan. 16, 2014

(30) Foreign Application Priority Data

Mar. 25, 2009    (JP) ................................. 2009-073998

(51) Int. Cl.
*C12Q 1/68*    (2006.01)

(52) U.S. Cl.
CPC ............ *C12Q 1/6886* (2013.01); *C12Q 1/6837* (2013.01); *C12Q 2600/112* (2013.01); *C12Q 2600/118* (2013.01)

(58) Field of Classification Search
USPC ........................................................ 435/6.14
See application file for complete search history.

(56) References Cited

FOREIGN PATENT DOCUMENTS

JP    2005-304496    11/2005
JP    2008-118866    5/2008

OTHER PUBLICATIONS

Pimkhaokham et al. Cancer Science; vol. 91, Issue 11, pp. 1126-1133, Nov. 2000.*
Ueki et al. Oncogene (2008) 27, 5672-5683.*
Nguyen et al. Cancer Sci. May 2007;98(5):740-6. Epub Mar. 28, 2007.*
Nguyen et al. Cancer Sci. May 2007; 98(5):740-6. Epub Mar. 28, 2007.*
Kanamoto et al.Journal of Surgical Oncology 1999;72:94-98.*
Brown et al., "Identification and characterization of Smyd2: a split SET/MYND domain-containing histone H3 lysine 36-specific methyltransferase that interacts with the Sin3 histone deacetylase complex", Molecular Cancer, vol. 5, No. 26, XP-002616236, Jun. 28, 2006.
Extended European Search Report, dated Jan. 24, 2011, for European Application No. 10157735.1.
Huang et al., "Repression of p53 activity by Smyd2-mediated methylation", Nature, vol. 444, No. 7119, pp. 629-632, XP-002616235, Nov. 30, 2006.
Japanese Office Action dated Aug. 20, 2013 for Japanese Application No. 2009-073998 with partial English translation.

(Continued)

*Primary Examiner* — Suryaprabha Chunduru
*Assistant Examiner* — Sahana Kaup
(74) *Attorney, Agent, or Firm* — Birch, Stewart, Kolasch & Birch, LLP

(57) ABSTRACT

An object of the present invention is to provide a method for detecting cancer and an agent for suppressing cell growth by identification of genes showing behaviors characteristic in cancer such as esophageal carcinoma. The present invention provides a method for detecting cancer, which comprises detecting canceration through detection of amplification of at least one gene existing in an 1q32-1q41 chromosomal region in a specimen.

3 Claims, 12 Drawing Sheets
(7 of 12 Drawing Sheet(s) Filed in Color)

(56) References Cited

OTHER PUBLICATIONS

Atiphan Pimkhaokham et al.: Nonrandom chromosomal imbalances in esophageal squamous cell carcinoma cell lines: possible involvement of the ATF3 and CENPF genes in the 1q32 amplicon; Japanese Journal of Cancer Research; vol. 91; No. 11; Nov. 2000; ppl. 1126/1133.

Herman van Dekken et al.; Genomic analysis of early adenocarcinoma of the esophagus or gastroesophageal junction: Tumor progression is associated with alteration of 1q and 8p sequences; Genes Chromosomes & Cancer; vol. 45, No. 5: May 2006; pp. 516-525.

Julia J. Li et al.; Overexpression of retinoic acid-regulated nuclear matrix-associated protein (RAMP) induces cell proliferation in gastric cancer: Potential oncogenic role of RAMP in gastric carcinogenesis; Gastroenterology: vol. 134: No. 4; Suppl. 1: Apr. 2008: p. A386.

Partial European Search Report dated Oct. 21, 2010 issued in corresponding EP application No. 10157735.1.

Shuhei Komatsu et al.; Overexpression of SMYD2 relates to tumor cell proliferation and malignant outcome of esophageal squamous cell carcinoma; Carcinogenesis; vol. 30; No. 7: Jul. 2009: pp. 1139-1146.

T. Ueki et al.; Involvement elevated expression on multiple cell-cycle regulator, DTL/RAMP (denticieless/RA-regulated nuclear matrix associated protein), in the growth of breast cancer cells: Oncogene: vol. 27; No. 43: Sep. 2008: pp. 5672-5638.

* cited by examiner

```
                        SEQUENCE LISTING

<160> NUMBER OF SEQ ID NOS: 5

<210> SEQ ID NO 1
<211> LENGTH: 1685
<212> TYPE: DNA
<213> ORGANISM: human
<220> FEATURE:
<221> NAME/KEY: CDS
<222> LOCATION: (34)..(1335)

<400> SEQUENCE: 1
gggcacagcc ggcggccgcg ccccgccgcc acc atg agg gcc gag ggc ctc ggc      54
                                    Met Arg Ala Glu Gly Leu Gly
                                    1               5 ggc ctg gag cgc ttc tgc agc ccg ggc aaa ggc cgg ggg ctg cgg gct     102
Gly Leu Glu Arg Phe Cys Ser Pro Gly Lys Gly Arg Gly Leu Arg Ala
         10                  15                  20 ctg cag ccc ttc cag gtg ggg gac ttg ctg ttc tcc tgc ccg gcc tat     150
Leu Gln Pro Phe Gln Val Gly Asp Leu Leu Phe Ser Cys Pro Ala Tyr
     25                  30                  35 gcc tac gtg ctc acg gtc aac gag cgg ggc aac cac tgc gag tac tgc     198
Ala Tyr Val Leu Thr Val Asn Glu Arg Gly Asn His Cys Glu Tyr Cys
 40                  45                  50                  55 ttc acc agg aaa gaa gga ttg tcc aaa tgt gga aga tgc aag cag gca     246
Phe Thr Arg Lys Glu Gly Leu Ser Lys Cys Gly Arg Cys Lys Gln Ala
                 60                  65                  70 ttt tac tgc aat gtg gag tgt cag aaa gaa gat tgg ccc atg cac aag     294
Phe Tyr Cys Asn Val Glu Cys Gln Lys Glu Asp Trp Pro Met His Lys
             75                  80                  85 ctg gaa tgt tct ccc atg gtt gtt ttt ggg gaa aac tgg aat ccc tcg     342
Leu Glu Cys Ser Pro Met Val Val Phe Gly Glu Asn Trp Asn Pro Ser
         90                  95                 100 gag act gta aga cta aca gca agg att ctg gcc aaa cag aaa atc cac     390
Glu Thr Val Arg Leu Thr Ala Arg Ile Leu Ala Lys Gln Lys Ile His
    105                 110                 115 cca gag aga aca cct tcg gaa aaa ttg tta gct gtg aag gag ttt gaa     438
Pro Glu Arg Thr Pro Ser Glu Lys Leu Leu Ala Val Lys Glu Phe Glu
120                 125                 130                 135 tca cat ctg gat aag tta gac aat gag aag aag gat ttg att cag agt     486
Ser His Leu Asp Lys Leu Asp Asn Glu Lys Lys Asp Leu Ile Gln Ser
                140                 145                 150 gac ata gct gct ctc cat cac ttt tac tcc aag cat ctc gga ttc cct     534
Asp Ile Ala Ala Leu His His Phe Tyr Ser Lys His Leu Gly Phe Pro
            155                 160                 165 gac aat gat agc ctc gta gta ctc ttt gca cag gtt aac tgt aat ggc     582
Asp Asn Asp Ser Leu Val Val Leu Phe Ala Gln Val Asn Cys Asn Gly
        170                 175                 180 ttc aca att gaa gat gaa gaa ctt tct cat ttg gga tca gcg ata ttt     630
Phe Thr Ile Glu Asp Glu Glu Leu Ser His Leu Gly Ser Ala Ile Phe
    185                 190                 195 cct gat gtt gca ttg atg aat cat agc tgt tgc ccc aat gtc att gtg     678
Pro Asp Val Ala Leu Met Asn His Ser Cys Cys Pro Asn Val Ile Val
200                 205                 210                 215 acc tac aaa ggg acc ctg gca gaa gtc aga gct gta cag gaa atc aag     726
Thr Tyr Lys Gly Thr Leu Ala Glu Val Arg Ala Val Gln Glu Ile Lys
```

```
                Thr Tyr Lys Gly Thr Leu Ala Glu Val Arg Ala Val Gln Glu Ile Lys
                                220                 225                 230 ccg gga gag gag gtt ttt acc agc tat att gat ctc ctg tac cca acg       774
Pro Gly Glu Glu Val Phe Thr Ser Tyr Ile Asp Leu Leu Tyr Pro Thr
            235                 240                 245 gaa gat aga aat gac cgg tta aga gat tct tat ttc ttt acc tgt gag       822
Glu Asp Arg Asn Asp Arg Leu Arg Asp Ser Tyr Phe Phe Thr Cys Glu
            250                 255                 260 tgc cag gag tgt acc acc aag gac aag gat aag gcc aag gtg gaa atc       870
Cys Gln Glu Cys Thr Thr Lys Asp Lys Asp Lys Ala Lys Val Glu Ile
        265                 270                 275 cgg aag ctc agc gat ccc cca aag gca gaa gcc atc cga gac atg gtc       918
Arg Lys Leu Ser Asp Pro Pro Lys Ala Glu Ala Ile Arg Asp Met Val
280                 285                 290                 295 aga tat gca cgc aac gtc att gaa gag ttc cgg agg gcc aag cac tat       966
Arg Tyr Ala Arg Asn Val Ile Glu Glu Phe Arg Arg Ala Lys His Tyr
                300                 305                 310 aaa tcc cct agt gag ctg ctg gag atc tgc gag ctc agc cag gag aag      1014
Lys Ser Pro Ser Glu Leu Leu Glu Ile Cys Glu Leu Ser Gln Glu Lys
            315                 320                 325 atg agc tct gtg ttt gag gac agt aac gtg tac atg ttg cac atg atg      1062
Met Ser Ser Val Phe Glu Asp Ser Asn Val Tyr Met Leu His Met Met
            330                 335                 340 tac cag gcc atg ggt gtc tgc ttg tac atg cag gac tgg gaa gga gcc      1110
Tyr Gln Ala Met Gly Val Cys Leu Tyr Met Gln Asp Trp Glu Gly Ala
345                 350                 355 ctg caa tat gga cag aaa atc att aag ccc tac agt aag cac tat cct      1158
Leu Gln Tyr Gly Gln Lys Ile Ile Lys Pro Tyr Ser Lys His Tyr Pro
360                 365                 370                 375 ttg tac tcc ctc aac gtg gcc tcc atg tgg ttg aag cta ggg aga ctc      1206
Leu Tyr Ser Leu Asn Val Ala Ser Met Trp Leu Lys Leu Gly Arg Leu
                380                 385                 390 tac atg ggc ctg gaa cac aaa gcc gca ggg gag aaa gcc ctg aag aag      1254
Tyr Met Gly Leu Glu His Lys Ala Ala Gly Glu Lys Ala Leu Lys Lys
            395                 400                 405 gcc att gca atc atg gaa gta gct cac ggc aaa gat cat cca tat att      1302
Ala Ile Ala Ile Met Glu Val Ala His Gly Lys Asp His Pro Tyr Ile
            410                 415                 420 tct gag atc aaa cag gaa att gaa agc cac tga aactatgcag catttcagtt   1355
Ser Glu Ile Lys Gln Glu Ile Glu Ser His
            425                 430 ttcatttaaa cacttagttc agaaacctta aaggatttga atatttcaaa ttgcacacgt   1415
cactccagca tctctgtaaa ataattggaa tgaaaatact tcttgcactt aaacactgca   1475
catgccgtac tttgaggtta gtctgaatct tgaactttaa taccaaatta attttgaatg   1535
cttttgtttc ctaagagata atggcatggt ttcatatgtt atactttgga cagacagagt   1595
tttaaaaatg gaattatttt ttctttcatg cctcttgtaa tgttctgaac aaacttgaat   1655
gatgaaagta ttaaagagat atcagtattt                                    1685

<210> SEQ ID NO 2
<211> LENGTH: 433
<212> TYPE: PRT
<213> ORGANISM: human

<400> SEQUENCE: 2

Met Arg Ala Glu Gly Leu Gly Gly Leu Glu Arg Phe Cys Ser Pro Gly
1               5                   10                  15

Lys Gly Arg Gly Leu Arg Ala Leu Gln Pro Phe Gln Val Gly Asp Leu
```

```
            20                  25                  30
Leu Phe Ser Cys Pro Ala Tyr Ala Tyr Val Leu Thr Val Asn Glu Arg
         35                  40                  45
Gly Asn His Cys Glu Tyr Cys Phe Thr Arg Lys Glu Gly Leu Ser Lys
         50                  55                  60
Cys Gly Arg Cys Lys Gln Ala Phe Tyr Cys Asn Val Glu Cys Gln Lys
 65                  70                  75                  80
Glu Asp Trp Pro Met His Lys Leu Glu Cys Ser Pro Met Val Val Phe
                 85                  90                  95
Gly Glu Asn Trp Asn Pro Ser Glu Thr Val Arg Leu Thr Ala Arg Ile
                100                 105                 110
Leu Ala Lys Gln Lys Ile His Pro Glu Arg Thr Pro Ser Glu Lys Leu
                115                 120                 125
Leu Ala Val Lys Glu Phe Glu Ser His Leu Asp Lys Leu Asp Asn Glu
            130                 135                 140
Lys Lys Asp Leu Ile Gln Ser Asp Ile Ala Ala Leu His His Phe Tyr
145                 150                 155                 160
Ser Lys His Leu Gly Phe Pro Asp Asn Asp Ser Leu Val Val Leu Phe
                165                 170                 175
Ala Gln Val Asn Cys Asn Gly Phe Thr Ile Glu Asp Glu Glu Leu Ser
                180                 185                 190
His Leu Gly Ser Ala Ile Phe Pro Asp Val Ala Leu Met Asn His Ser
            195                 200                 205
Cys Cys Pro Asn Val Ile Val Thr Tyr Lys Gly Thr Leu Ala Glu Val
210                 215                 220
Arg Ala Val Gln Glu Ile Lys Pro Gly Glu Glu Val Phe Thr Ser Tyr
225                 230                 235                 240
Ile Asp Leu Leu Tyr Pro Thr Glu Asp Arg Asn Asp Arg Leu Arg Asp
                245                 250                 255
Ser Tyr Phe Phe Thr Cys Glu Cys Gln Glu Cys Thr Thr Lys Asp Lys
                260                 265                 270
Asp Lys Ala Lys Val Glu Ile Arg Lys Leu Ser Asp Pro Pro Lys Ala
            275                 280                 285
Glu Ala Ile Arg Asp Met Val Arg Tyr Ala Arg Asn Val Ile Glu Glu
            290                 295                 300
Phe Arg Arg Ala Lys His Tyr Lys Ser Pro Ser Glu Leu Leu Glu Ile
305                 310                 315                 320
Cys Glu Leu Ser Gln Glu Lys Met Ser Ser Val Phe Glu Asp Ser Asn
                325                 330                 335
Val Tyr Met Leu His Met Met Tyr Gln Ala Met Gly Val Cys Leu Tyr
            340                 345                 350
Met Gln Asp Trp Glu Gly Ala Leu Gln Tyr Gly Gln Lys Ile Ile Lys
            355                 360                 365
Pro Tyr Ser Lys His Tyr Pro Leu Tyr Ser Leu Asn Val Ala Ser Met
            370                 375                 380
Trp Leu Lys Leu Gly Arg Leu Tyr Met Gly Leu Glu His Lys Ala Ala
385                 390                 395                 400
Gly Glu Lys Ala Leu Lys Lys Ala Ile Ala Ile Met Glu Val Ala His
                405                 410                 415
Gly Lys Asp His Pro Tyr Ile Ser Glu Ile Lys Gln Glu Ile Glu Ser
            420                 425                 430
His
```

```
<210> SEQ ID NO 3
<211> LENGTH: 21
<212> TYPE: RNA
<213> ORGANISM: Artificial Sequence
<220> FEATURE:
<223> OTHER INFORMATION: Synthetic siRNA

<400> SEQUENCE: 3
gcaaagauca uccauauauu u                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic siRNA

<400> SEQUENCE: 4
cguacgcgga auacuucgau u                                              21

<210> SEQ ID NO 5
<211> LENGTH: 14
<212> TYPE: PRT
<213> ORGANISM: Artificial Sequence
<220> FEATURE:
<223> OTHER INFORMATION: Chemically synthesized anti-SMYD2 polyclonal
      antibody

<400> SEQUENCE: 5

His Pro Tyr Ile Ser Glu Ile Lys Gln Glu Ile Glu Ser His
1               5                   10
```

METHOD FOR DETECTING ESOPHAGEAL CARCINOMA AND AGENT FOR SUPPRESSING ESOPHAGEAL CARCINOMA

TECHNICAL FIELD

The present invention relates to a method for detecting cancer such as esophageal carcinoma and an agent for suppressing cancer.

BACKGROUND ART

Esophageal carcinoma is epithelially derived tumor (cancer) that occurs in the esophagus. 10,000 or more people in Japan develop esophageal carcinoma annually. The male to female ratio is about 6:1, indicating that the disease occurs more often in men. Esophageal carcinoma is the sixth most common form of cancer in men. The annual death toll ranges from 9,000 to 10,000 in Japan, accounting for 3% of total cancer cases. Esophageal carcinoma is histologically classified into esophageal squamous cell carcinoma (ESCC) and adenocarcinoma. The former is caused by canceration of mucosal epithelial cells of the esophagus, accounting for 90% or more of all the esophageal carcinoma cases. The latter is caused by canceration of Barrett esophagus cells. These cases together account for 95% or more of all the esophageal carcinoma cases.

Esophageal carcinoma even at the stage of low invasion depth frequently results in lymph node metastasis. Also the esophagus anatomically differs from other digestive system organs, having no chorionic membrane (outer membrane). Hence, the carcinoma relatively easily invades the surrounding tissues. Even now the 5-year survival rate is about 30% on average, suggesting its extremely poor prognosis among other GI cancers (gastric cancer: 60%; large-bowel cancer: 70%; liver cancer: 40%; and pancreatic cancer: 15%). Therefore, further improvement in diagnostic and therapeutic technology has been desired. As diagnostic procedures, imaging studies using esophagography, endoscopy, ultrasonic endoscopy, CT (computer tomography), PET (positron emission tomography devices), or the like and methods based on tumor markers such as SCC (squamous cell carcinoma related antigen) and CEA (carcinoembryonic antigen) are known. However, currently no promising biomarker exists at the sites of clinical practice that enables early diagnosis of the malignancy of esophageal carcinoma or a prediction of its recurrence. Meanwhile, regarding treatment, endoscopic demucosation or surgical treatment is generally carried out. In cases for which radical surgery is difficult, multidisciplinary treatment using chemotherapy or chemoradiotherapy is carried out before or after surgery. However, currently, biomarkers that enable prediction of the sensitivity to treatment do not exist. Also, clinically applied drugs for molecular target therapy, which have been revealed to be effective against breast cancer, large-bowel cancer, lung cancer and the like still do not currently exist for esophageal carcinoma.

As described above, (1) further detailed elucidation of the molecular mechanisms involved in the occurrence and development of esophageal carcinoma; (2) search for therapeutic target molecules against advanced and/or recurrent esophageal carcinoma; and (3) development of diagnostic•prognosis predictive markers for determination of a course of treatment are thought to be urgent problems.

It has been reported to date that decreased expression of Low Density Lipoprotein Receptor-Related Protein 1B (LRP1B) or deletion of the genome gene can be used for diagnosis of esophageal carcinoma (JP Patent Publication (Kokai) No. 2005-304496 A). It has also been reported that decreased expression of human Cellular Retinoic Acid Binding Protein 1 (human CRABP1) or deletion of the genome gene can be used for diagnosis of esophageal carcinoma (JP Patent Publication (Kokai) No. 2008-118866 A). However, elucidation of the molecular mechanism of ESCC has remained insufficient and further analysis therefor has been required.

SUMMARY OF THE INVENTION

Elucidation of the mechanism for canceration of the esophagus at the gene level enables early detection of canceration of esophagus-derived cells at the gene level, diagnosis of malignancy of esophageal carcinoma, and suppression of the progression of esophageal carcinoma. Moreover, such elucidation will also enable selection and development of drugs based on the mechanism or establishment of therapeutic methods. Specifically, the problem can be addressed through identification of genes showing behaviors characteristic in esophageal squamous cell carcinoma and technical studies mainly concerning genes. Hence, an object to be achieved by the present invention is to provide a method for detecting cancer and an agent for suppressing cell growth by identification of genes showing behaviors characteristic in cancer such as esophageal carcinoma.

Comparative Genomic Hybridization (CGH) is the best method since it allows convenient and rapid analysis of amplification and deletion of many genes in the genome or analysis of genetic abnormalities associated with inactivation of genes. The present inventors have analyzed abnormalities of various cancer genes with the use of MCG Whole Genome-4500 (Inazawa J., et al., Cancer Sci. 95, 559-563, 2004) obtained via selection of 4500 types of BAC/PAC DNA to be mounted on CGH arrays in order to analyze abnormalities of genes in the genome involved in canceration, malignant alteration of cancer, and the like. In this manner, the present inventors have detected cancer-associated genes. At this time, the present inventors have conducted analyses using a further detailed analysis method (High-density oligo-array CGH method) and the FISH method for amplification regions detected using MCG Whole Genome—4500. In this ways, they have succeeded in identification of abnormalities in the copy number of 1q32-1q41 including a cancer-associated gene that accelerates canceration of ESCC-derived cells; that is, the SMYD2 (SET and MYND domain containing 2) gene. Furthermore, the present inventors have clarified overexpression of the SMYD2 protein by immunohistochemical analysis using 43 types of ESCC cell lines and clinical specimens from 153 cases. Thus, the present inventors have successfully discovered that in the cases of ESCC cell lines, enhanced SMYD2 protein expression significantly accelerates ESCC cell growth and that the suppression of SMYD2 gene transcripts results in significantly decreased ESCC cell growth. The analysis of clinical specimens revealed that patients expressing SMYD2 at high levels showed extremely poor prognosis and that SMYD2 is an independent prognostic factor. The present invention has been completed based on these findings.

Thus, the present invention provides the followings.

(1) A method for detecting cancer, which comprises detecting canceration through detection of amplification of at least one gene existing in an 1q32-1q41 chromosomal region in a specimen.

(2) The method for detecting cancer according to (1), wherein the gene is at least one gene selected from among DTL, C1orf75, ATF3, SNFT, NSL1, FLVCR, ANGEL2, SMYD2, PTPN14, and CENPF.
(3) The method for detecting cancer according to (1), wherein an amplification index is 1.32 or more times greater than that of a normal specimen.
(4) The method for detecting cancer according to (3), wherein the gene is SMYD2.
(5) The method for detecting cancer according to (1), wherein the specimen is a tissue from the esophagus.
(6) The method for detecting cancer according to (1), wherein the cancer is esophageal carcinoma.
(7) The method for detecting cancer according to (1), wherein a genetic change is detected by using a DNA chip method, a Southern blot method, a Northern blot method, a real-time RT-PCR method, a FISH method, a CGH method, an array CGH method, a Bisulfite Sequence method, or a COBRA method.
(8) A method for detecting cancer, which comprises detecting the amount of a protein that is translated from at least one gene selected from among DTL, C1orf75, ATF3, SNFT, NSL1, FLVCR, ANGEL2, SMYD2, PTPN14, and CENPF in a specimen.
(9) The method for detecting cancer according to (8), wherein the amount of a protein is detected by an immunohistochemical method.
(10) The method for detecting cancer according to (1), wherein canceration including malignancy within a specimen, is detected.
(11) The method for detecting cancer according to (1), wherein canceration is detected by using SMYD2 expression and p53 expression as indices.
(12) An agent for suppressing cell growth, which comprises an siRNA of an SMYD2 gene, an antisense oligonucleotide of an SMYD2 gene, or a loss-of-function-type SMYD2 gene.
(13) A method for suppressing cell growth, which comprises administering an siRNA of an SMYD2 gene, an antisense oligonucleotide of an SMYD2 gene, or a loss-of-function-type SMYD2 gene to cells in vitro.

The present invention makes it possible to precisely grasp canceration and malignancy in cell specimens from the esophagus. Also, the present invention can suppress the growth of esophageal carcinoma through inactivation of the SMYD2 gene.

BRIEF DESCRIPTION OF THE DRAWINGS

The patent or application file contains at least seven drawings executed in color. Copies of this patent or patent application publication with color drawings will be provided by the office upon request and payment of the necessary fee.

FIG. 12 also shows the relationship between SMYD2 and p53 protein expression and the survival rates.

PREFERRED EMBODIMENTS OF THE INVENTION

Figure 1:
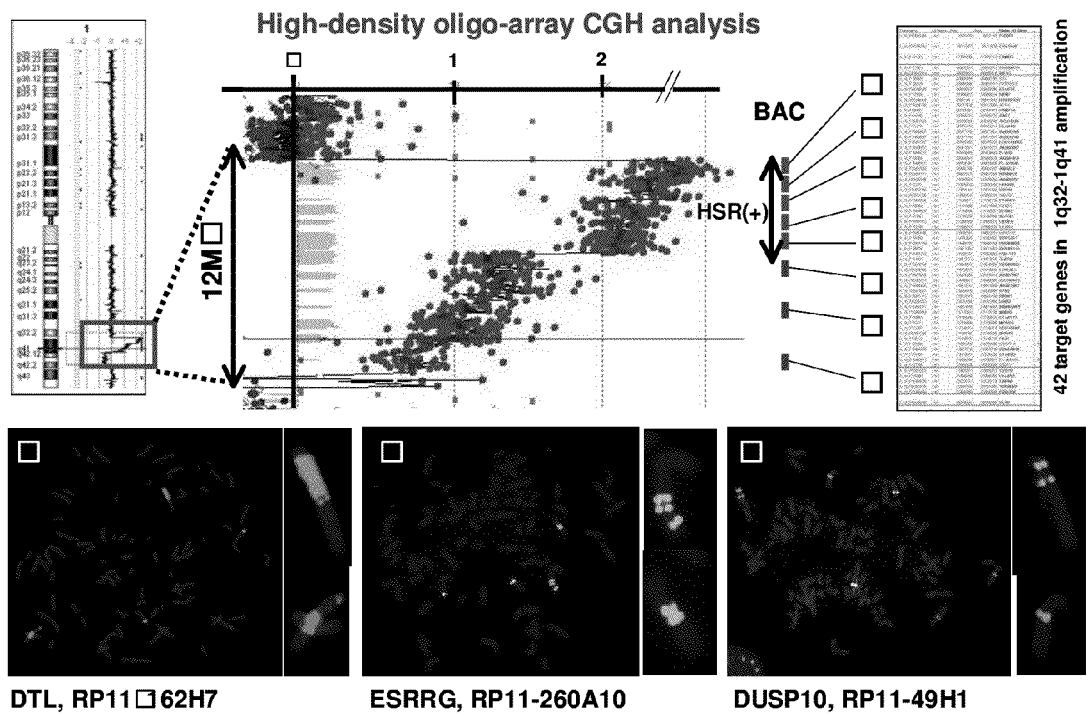
FIG. 1 shows an amplicon map of the 1q32-1q41 gene region of ESCC cell lines. The upper left side shows the results of analyzing the 1q32-1q41 region using an Agilent 244K high-density oligo-array (the horizontal axis denotes the LOG 10 value of the number of copies). The upper right side shows 7 types of BAC region and 42 types of gene contained in the regions used for FISH analysis (BAC-1 to 7:1 RP11-162H7, DTL, and 1q32.3 green (control: RP11-351H16, 1q41 red); 2 RP11-90A5, ATF3, and 1q32.3 green (control: RP11-351H16 and 1q41 red); 3 RP11-262H5, CENPF, and 1q41 green (control: RP11-351H16 and 1q41 red); 4 RP11-74E6, SMYD2, and 1q41 green (control: RP11-82D16 and 1p36.3 red); 5 RP11-157G15, GPATC2, and 1q41 green (control: RP11-351H16 and 1q41 red); 6: RP11-170J15 and TGFβ2 1q41 green (control: RP11-351H16, 1q41red); and 7: RP11-49H1, DUSP10, and 1q41 green (control: RP11-351H16, 1q41 red)). Photographs in the lower column show the results of FISH analysis using BAC-1, 4, 5, and 8 as probes.

The present invention is further described in detail as follows.

(1) Method for Detecting Cancer

The method for detecting cancer according to the present invention is characterized by detecting amplification of at least one gene existing in a 1q32-1q41 chromosomal region (hereinafter also referred to as the chromosomal region of the present invention) in a specimen. Preferably, a gene to be detected herein is at least one gene (hereinafter, also referred to as the gene of the present invention) selected from among DTL, C1orf75, ATF3, SNFT, NSL1, FLVCR, ANGEL2, SMYD2, PTPN14, and CENPF, and is further preferably a SMYD2 gene. Also, in the present invention, cancer can also be detected by detecting the amount of a protein that is translated from at least one gene selected from among DTL, C1orf75, ATF3, SNFT, NSL1, FLVCR, ANGEL2, SMYD2, PTPN14, and CENPF in a specimen.

As described above, preferably, according to the present invention, malignancy of the cancer cells can be detected and esophageal carcinoma can be detected through detection of SMYD2 gene amplification or protein expression in esophageal carcinoma cells.

SMYD2 (SET AND MYND DOMAIN-CONTAINING PROTEIN 2) is located at 1q41, encoding a protein comprising 433 amino acids. SMYD2 contains a SET domain comprising a cysteine-rich domain connected to a MYND domain, which is divided into two by the MYDN domain. Mammalian SMYD2 has been reported to have functions of: (1) dimethylating lys36 of histone H3, (2) suppressing transcription from an SV40 reporter plasmid, (3) decreasing growth of mouse fibroblasts when exogenous SMYD2 expression takes place, and the like (Brown M A et al. Mol Cancer 2006). On the other hand, It is reported (Huang J et al. Nature 2006) that SMYD2 may function as a cancer gene by methylating Lysine 370 of p53 as Lysine methyltransferase, so as to inhibit the tumor-suppressing functions of p53. However, there exists no report actually suggesting the correlation between the SMYD2 gene and human cancer.

As described above, the detection method (e.g., array CGH method) is characterized by detecting the chromosomal region of the present invention and gene amplification of the present invention in esophagus-derived cells or esophageal carcinoma.

Esophagus-derived cells or esophageal carcinoma to be subjected to detection of the chromosomal region of the present invention and gene amplification of the present invention are preferably biopsy tissue cells of a specimen donor.

Such biopsied tissue cells of specimen donors may be either the esophagus-derived cells of a healthy subject or the cancerous tissues of an esophagus carcinoma patient. In practice, examples of a major target tissue specimen that can be used herein include: a tissue obtained from a lesion in which suspected malignant transformation is observed by a test or the like; and a esophagus carcinoma tissue that has been confirmed to be derived from esophagus carcinoma and thus must be subjected to determination of malignancy or the stage progression of the esophagus carcinoma.

When the amplification of the chromosomal regions of the present invention and the genes of the present invention is confirmed by the method of the present invention in the "pathologic tissue of esophagus having a lesion suspected to be malignant as confirmed by a test or the like", it is revealed that the pathologic tissue is undergoing a process toward canceration or is already in the malignant state, and that the malignancy thereof is increasing. Thus, the need to carry out immediate full-scale treatment (such as lesion removal by operation or the like and full-scale chemotherapy) is demonstrated. Moreover, when the amplification of the chromosomal regions of the present invention and the genes of the present invention is confirmed in the "tissue that is confirmed to be esophagus carcinoma and for which determination of malignancy or the stage progression thereof is required", it is revealed that the malignancy of the cancer tissue is increasing. Hence, the need to carry out immediate full-scale treatment (such as lesion removal by operation or the like or full-scale chemotherapy) is demonstrated. A esophagus carcinoma tissue sampled as a specimen can be subjected to the present detection method after applying necessary treatment such as with the preparation of DNA or RNA from the sampled tissue.

In the detection method of the present invention, the amplification of the chromosomal regions of the present invention and the genes of the present invention is detected in esophagus-derived cells or esophagus carcinoma cells as mentioned above, so that tumorigenic transformation of said cells is detected and classified.

Next, detection of the amplification of the chromosomal regions of the present invention and the genes of the present invention is described below.

Examples of a typical method by which amplification of the chromosomal regions of the present invention and the genes of the present invention can be directly detected include a CGH (Comparative Genomic Hybridization) method and a FISH (Fluorescence in situ hybridization) method. According to the detection method in this embodiment, BAC (Bacterial Artificial Chromosome) DNA, YAC (Yeast Artificial Chromosome) DNA, or PAC (P1-drived Artificial Chromosome) DNA (hereinafter, also referred to as BAC DNA, for example) having the chromosomal regions of the present invention and the genes of the present invention is labeled and then FISH is performed, so that the presence or the absence of the chromosomal regions of the present invention and the genes of the present invention can be detected. Specifically, examples of BAC DNA having SMYD2 gene may include RP11-74E6 and the like.

It is preferable and practical to carry out the method in the above embodiment with the use of a genomic DNA-immobilized matrix.

The amount of BAC DNA or the like obtained in a conventional manner is so small that a large number of genomic DNA-immobilized matrices cannot be produced for practical application. Thus, it is necessary to obtain gene amplification products of such DNA. (A gene amplification process for this purpose is referred to as "infinite amplification" in some cases.) Upon infinite amplification, BAC DNA or the like is first digested with a four-base recognition enzyme such as Rsa I, Dpn I, Hae III, or the like, followed by ligation with the addition of an adaptor. An adaptor comprises oligonucleotides having 10 to 30 bases and preferably 15 to 25 bases. Double strands of such adaptor have sequences complementary to each other. After annealing, the 3' end of one of the oligonucleotides, at which a blunt end is formed, must be phosphorylated. Next, a primer having a sequence identical to the other oligonucleotide of the adaptor is used for amplification via PCR (polymerase chain reaction). Thus, infinite amplification can be carried out. Meanwhile, it is also possible to use, as a detection probe, an aminated oligonucleotide comprising 50 to 70 bases, which is inherent to BAC DNA or the like.

BAC DNAs or the like subjected to infinite amplification are immobilized on a matrix and preferably on a solid matrix. Accordingly, a desired DNA-immobilized matrix can be produced. An example of such solid matrix is more preferably a glass plate. Such a solid matrix made of glass or the like is more preferably coated via adhesion with poly-L-lysine, aminosilane, gold, aluminium, or the like.

The concentration of DNA subjected to infinite amplification to be spotted on a matrix is preferably 10 pg/µl to 5 µg/µl and more preferably 1 ng/µl to 200 ng/µl. The amount of the same to be spotted on the matrix is preferably 1 nl to 1 µl and more preferably 10 nl to 100 nl. In addition, the size and the shape of each spot that is immobilized on the matrix are not particularly limited. In terms of size, such spot may have a diameter ranging from 0.01 to 1 mm, for example. In addition, the shape of such spot may be a circle or ellipse from an overhead view. The thickness of a dry spot is not particularly limited; however, it may be 1 to 100 µm. Further, the number of spots is not particularly limited; however, it may be 10 to 50,000 spots and more preferably 100 to 5,000 spots on the matrix used. DNAs are spotted singly to quadruplicate. However, preferably, DNAs are spotted in duplicate or triplicate.

Regarding preparation of dry spots, it is possible to produce dry spots by, for example, spotting BAC DNAs or the like subjected to infinite amplification on a matrix with the use of a spotter, forming a plurality of spots thereon, and drying the spots. Examples of a spotter that can be used include an inkjet printer, a pin-array printer, and a bubble jet (trademark) printer. An inkjet printer is desirably used. For instance, GENESHOT (NGK INSULATORS; Nagoya, Japan) or the like can be used.

As described above, it is possible to produce a desired DNA-immobilized matrix by immobilizing BAC DNAs or the like subjected to infinite amplification onto a matrix, and preferably, onto a solid matrix.

In addition, an example of a means of directly detecting the deletion of the chromosomal regions of the present invention and the genes of the present invention is the Southern blot method. The Southern blot method is a method for detecting the presence of the gene of interest in a specimen by separating and immobilizing genomic DNA obtained from the specimen and detecting hybridization of such genomic DNA with the gene of interest.

Furthermore, amplification of a gene can be detected by quantitative analysis of expression of mRNA which is derived from a gene of interest.

Furthermore, the amplification of the gene of interest can also be directly detected by the PCR method. Genomic DNA is separated from a test sample, and is amplified using a primer which can amplify a full length of said gene or a part thereof, and the amplified product is quantified so that the amplification of the gene can be detected. In the present invention, cancer can be detected by detecting the amount of a protein that is translated from at least one gene selected from among DTL, C1orf75, ATF3, SNFT, NSL1, FLVCR, ANGEL2, SMYD2, PTPN14, and CENPF. The amount of a protein can be detected by an immunohistochemical method. The immunohistochemical method can be carried out in accordance with conventional protocols.

When the gene of the present invention (for example, SMYD2 gene) is handled, cDNA obtained from a cultured cell in accordance with a technique known in the art or cDNA enzymatically synthesized via PCR based on the nucleotide sequence as shown in SEQ ID NO: 1 (when SMYD2 gene is used) in the Sequence Listing of the present application may be used. SEQ ID NO: 1 in the Sequence Listing of the present application shows a nucleotide sequence of cDNA (NM_020197) of MNYD2, and SEQ ID NO: 1 shows an amino acid sequence of MNYD2. When DNA having the nucleotide sequence as shown in SEQ ID NO: 1 is obtained via PCR, PCR is carried out using a human chromosome DNA or cDNA library as a template and a primer designed to be capable of amplifying the nucleotide sequence as shown in SEQ ID NO: 1. The PCR-amplified DNA fragment can be cloned into an adequate vector that is capable of amplification in an *E. coli* host or the like.

Manipulations such as preparation of detection probes or primers for the gene of the present invention and cloning of target genes are already known to those skilled in the art. For example, such manipulations can be performed according to methods described in Molecular Cloning: A Laboratory Manual, $2^{nd}$ Ed., Cold Spring Harbor Laboratory, Cold Spring Harbor, N.Y., 1989, Current Protocols in Molecular Biology, Supplement 1 to 38, John Wiley & Sons (1987-1997), or the like.

(2) Method for Suppressing Cell Growth and Cell Growth Suppressing Agent

According to the present invention, there are provided a method for suppressing cell growth which comprises introducing an siRNA, an shRNA, an antisense oligonucleotide, or a loss-of-function type gene of at least one gene which is selected from DTL, C1orf75, ATF3, SNFT, NSL1, FLVCR, ANGEL2, SMYD2, PTPN14, and CENPF into cells in vitro, and a cell growth suppressing agent which comprises said siRNA, shRNA, antisense oligonucleotide, or loss-of-function type gene.

siRNA is a double-strand RNA having a length of about 20 nucleotides (for example, 21 to 23 nucleotides) or shorter. Expression of such an siRNA in a cell enables to suppress the expression of a gene targeted by the siRNA (DTL, C1orf75, ATF3, SNFT, NSL1, FLVCR, ANGEL2, SMYD2, PTPN14, and CENPF in the present invention).

The siRNA to be used in the present invention may take any form as long as it is capable of inducing RNAi. Here, the term "siRNA" is an abbreviation for "short interfering RNA", which refers to a short-chain double-strand RNA of 10 nucleotides or longer obtained by: chemical or biochemical synthesis in an artificial manner; in vivo synthesis; or in vivo degradation of double-strand RNA of about 40 nucleotides or longer. The siRNA normally has a structure comprising 5'-phosphoric acid and 3'-OH, where the 3' terminal projects by about 2 nucleotides. A specific protein binds to the siRNA to form RISC(RNA-induced-silencing-complex). This complex recognizes mRNA having the homologous sequence to that of siRNA and binds thereto. Then, the mRNA is cleaved at the central part of the siRNA with an RNase III-like enzymatic activity.

The siRNA sequence and the mRNA sequence being the target of cleavage preferably match 100%. However, such 100% match is not always required, when unmatched nucleotides are located away from the central part of the siRNA. This is because the RNAi cleaving activity often partially remains.

Preferably, the homologous region between the siRNA nucleotide sequence and the nucleotide sequence of the DTL, C1orf75, ATF3, SNFT, NSL1, FLVCR, ANGEL2, SMYD2, PTPN14, and CENPF gene whose expression has to be suppressed, does not include the translation initiation region of the concerned gene. Since various transcriptional factors and translational factors are predicted to bind to the translation initiation region, it is anticipated that the siRNA be unable to effectively bind to the mRNA, leading to lowered effect. Accordingly, the homologous sequence is preferably away from the translation initiation region of the concerned gene by 20 nucleotides, and more preferably by 70 nucleotides. The homologous sequence may be, for example, a sequence in the vicinity of the 3' terminal of the concerned gene.

According to another aspect of the present invention, an shRNA (short hairpin RNA) comprising a short hairpin structure having a projection at the 3' terminal may also be used as a factor which can suppress the expression of a target gene through RNAi. The term shRNA refers to a molecule of about 20 or more nucleotides, in which the single-strand RNA includes partially palindromic nucleotide sequences to thereby have a double-strand structure within the molecule, forming a hairpin-like structure. Such an shRNA is broken down into a length of about 20 nucleotides (typically 21 nucleotides, 22 nucleotides, and 23 nucleotides, for example) within a cell after being introduced into the cell, and thus is capable of inducing RNAi in a similar manner to that of siRNA. As described above, the shRNA induces RNAi in a similar manner to that of siRNA, and thus can be effectively used in the present invention.

The shRNA preferably has a projection at the 3' terminal. There is no particular limitation on the length of the double-strand portion, although it is preferably about 10 or more nucleotides, and more preferably about 20 or more nucleotides. Here, the projecting 3' terminal is preferably a DNA, more preferably a DNA of at least 2 or more nucleotides, and yet more preferably a DNA of 2 to 4 nucleotides.

As described above, in the present invention, siRNA or shRNA can be used as a factor which can suppress the expression of the DTL, C1orf 75, ATF3, SNFT, NSL1, FLVCR, ANGEL2, SMYD2, PTPN14, or CENPF gene through RNAi. The advantages of siRNA are such that: (1) RNA itself, even when introduced into a cell, is not incorporated into a chromosome of normal cell, and therefore the treatment do not cause any inheritable mutations and the safety is high; (2) it is relatively easy to chemically synthesize short-chain double-strand RNA, and the form of double-strand RNA is more stable; and the like. The advantages of shRNA are such that: treatment through long-term suppression of gene expression can be achieved by producing a vector which can transcribe shRNA within a cell and introducing such a vector into the cell; and the like.

The siRNA or shRNA to be used in the present invention which can suppress the expression of the DTL, C1orf75, ATF3, SNFT, NSL1, FLVCR, ANGEL2, SMYD2, PTPN14, or CENPF gene through RNAi, may be chemically synthesized in an artificial manner, and may also be produced through in vitro RNA synthesis using DNA of a hairpin structure in which a sense strand DNA sequence and an antisense strand DNA sequence are linked in opposite directions, with a T7 RNA polymerase. In the case of in vitro synthesis, antisense and sense RNAs can be synthesized from a template DNA using the T7 RNA polymerase and a T7 promoter. After in vitro annealing thereof, transfection of the resultant RNA into cells induces RNAi to suppress the expression of a target gene. Here, for example, transfection of such RNA into cells can be carried out by a calcium phosphate method or a method using various transfection reagents (such as oligofectamine, lipofectamine, and lipofection).

The abovementioned siRNA and shRNA are also useful as cell growth suppressing agents. The administration method of the cell growth suppressing agent of the present invention may include oral administration, parenteral administration (such as intravenous administration, intramuscular administration, subcutaneous administration, intradermal administration, transmucosal administration, intrarectal administration, intravaginal administration, local administration to affected area, and skin administration), and direct administration to affected area. The agent of the present invention, if used as a medical composition, may be mixed with a pharmaceutically acceptable additive as required. Specific examples of such a pharmaceutically acceptable additive include, but not limited to, an antioxidant, a preservative, a coloring agent, a flavoring agent, a diluent, an emulsifier, a suspending agent, a solvent, a filler, an extending agent, a buffer agent, a delivery vehicle, a diluting agent, a carrier, an excipient, and/or a pharmaceutical adjuvant.

The form of the pharmaceutical preparation of the agent of the present invention is not particularly limited, and examples thereof include a liquid agent, an injectable agent, and a sustained release agent. A solvent to be used for prescribing the agent of the present invention as the above pharmaceutical preparation may be either aqueous or non-aqueous.

Furthermore, the siRNA or shRNA serving as an active ingredient of the cell growth suppressing agent of the present invention can be administered in the form of a nonviral vector or a viral vector. In the case of a nonviral vector, there can be employed methods in which nucleic acid molecules are introduced using liposomes (such as a liposome method, an HVJ-liposome method, a cationic liposome method, a lipofection method, and a lipofectamine method), microinjection methods, methods in which nucleic acid molecules are transferred together with carriers (metal particles) into cells using a gene gun. If the siRNA or shRNA is administered in vivo using a viral vector, viral vectors such as a recombinant adenovirus and a recombinant retrovirus can be employed. Introduction of siRNA or shRNA gene into a cell or tissue can be achieved through introduction of DNA which expresses siRNA or shRNA into a detoxified DNA or RNA virus such as retrovirus, adenovirus, adeno-associated virus, herpes virus, vaccinia virus, poxvirus, poliovirus, Sindbis virus, Sendai virus, and SV40, followed by infection with the recombinant virus into the cell or tissue.

The dose of the cell growth suppressing agent of the present invention can be determined by those skilled in the art with a consideration of the purpose of administration, the disease severity, the age, weight, gender, and previous history of the patient, and the type of siRNA or shRNA serving as an active ingredient. The dose of siRNA or shRNA is not particularly limited, and examples thereof include about 0.1 ng/kg/day to about 100 mg/kg/day, and preferably about 1 ng/kg/day to about 10 mg/kg/day. RNAi effect is typically exerted for one to three days after the administration. Therefore, administration is preferably performed at a frequency of everyday to every third day. When an expression vector is used, the administration can be performed approximately once a week.

In the present invention, an antisense oligonucleotide can also be used as a cell growth suppressing agent. Antisense oligonucleotides to be used in the present invention are nucleotides that are complementary or hybridize to consecutive 5 to 100 nucleotide sequences within the DNA sequence of the DTL, C1orf75, ATF3, SNFT, NSL1, FLVCR, ANGEL2, SMYD2, PTPN14, or CENPF gene. Such an antisense oligonucleotide may be either DNA or RNA, or may also be modified as long as its functions remain unaffected. The term "antisense oligonucleotide" used in this description includes not only oligonucleotides wherein all nucleotides corresponding to nucleotides composing a predetermined DNA or mRNA region are complementary to their counterparts, but also oligonucleotides that contain some mismatching nucleotides, as long as such oligonucleotides can stably hybridize to DNA or mRNA.

In addition, the antisense oligonucleotides may be modified. After appropriate modification, resulting modified antisense oligonucleotides will be hardly degraded in vivo. This enables more stable inhibition of the target. Examples of such modified oligonucleotide include S-oligo type (phosphorothioate-type), C-5 thyazole type, D-oligo type (phosphodiester-type), M-oligo type (methylphosphonate-type), peptide nucleic acid type, phosphodiester binding type, C-5 propinyl pyrimidine type, 2-O-propylribose, and 2'-methoxyribose type antisense oligonucleotides. Furthermore, such antisense oligonucleotide may also be an antisense oligonucleotide wherein at least some of the oxygen atoms composing phosphate groups are substituted with sulfur atoms or otherwise modified. Such an antisense oligonucleotide is particularly excellent in terms of nuclease resistance, water solubility, and affinity for RNA. As such an antisense oligonucleotide wherein at least some of the oxygen atoms composing phosphate groups are substituted with sulfur atoms or otherwise modified, an S-oligo type oligonucleotide can be enumerated.

The number of nucleotides in such antisense oligonucleotide is preferably 50 or less and more preferably 25 or less. Too large number of nucleotides results in increased effort and cost in oligonucleotide synthesis and lowered yields. Furthermore, the number of nucleotides of such antisense oligonucleotide is 5 or more and preferably 9 or more. A number of nucleotides of 4 or less is undesirable because of the resulting lowered specificity to a target gene.

Such antisense oligonucleotide (or a derivative thereof) can be synthesized by a usual method. For example, an antisense oligonucleotide or a derivative thereof can be easily synthesized using a commercially available DNA synthesizer (such as one produced by Applied Biosystems). It can be obtained by a synthesis method such as a solid-phase synthesis method using phosphoroamidite or a solid-phase synthesis method using hydrogen phosphonate.

When an antisense oligonucleotide is used as a cell growth suppressing agent in the present invention, it is generally provided in the form of a medical composition containing the antisense oligonucleotide and additive(s) for pharmaceutical preparation (such as a carrier and an excipient). The antisense oligonucleotide can be administered as a medicament to mammals including humans. The route of administration for such an antisense oligonucleotide is not particularly limited and may be either of oral administration or parenteral administration (such as intramuscular administration, intravenous administration, subcutaneous administration, peritoneal administration, transmucosal administration in the nasal cavity or the like, and inhalation administration).

The form of the pharmaceutical preparation of such an antisense oligonucleotide is not particularly limited. Examples of the pharmaceutical preparation for oral administration include tablets, capsules, fine granules, powders, granules, liquids, and syrups. Examples of the pharmaceutical preparation for parenteral administration include injections, infusions, suppositories, inhalants, transmucosal absorption systems, transdermal absorption systems, nasal drops, and ear drops. The form of a drug containing the antisense oligonucleotide, additive(s) to be used for the pharmaceutical preparation, a method for producing the pharmaceutical preparation, and the like can be appropriately selected by those skilled in the art.

The dose of the antisense oligonucleotide can be appropriately determined with a comprehensive consideration of the gender, age, and weight of the patient, the symptom severity, the purpose of administration such as prevention or treatment, and the presence/absence of other complication symptoms. The dose is generally 0.1 µg/kg of body weight/day to about 100 mg/kg of body weight/day, and preferably 0.1 µg/kg of body weight/day to about 10 mg/kg of body weight/day.

Furthermore, in the present invention, a loss-of-function type gene of the DTL, C1orf75, ATF3, SNFT, NSL1, FLVCR, ANGEL2, SMYD2, PTPN14, or CENPF gene can also be used as a cell growth suppressing agent. The loss-of-function type gene refers to a mutated gene which causes loss of function of the corresponding gene. Specific examples thereof include genes which translate proteins lacking their original functions, generally called muteins, including those lacking at least one constituent amino acid(s), those having at least one constituent amino acid(s) replaced by other amino acid(s), and those added with at least one amino acid(s), within the amino acid sequence produced by the concerned gene.

When such a loss-of-function type gene is used as the cell growth suppressing agent, it can be produced by mixing the abovementioned gene serving as an active ingredient with a base that is commonly used for gene therapeutic agents. Moreover, when such a gene is incorporated into a viral vector, virus particles containing the recombinant vector are prepared, and are then mixed with a base that is commonly used for gene therapeutic agents.

As to the base, bases commonly used for injectable agents can be used. Examples thereof include: distilled water: salt solutions containing sodium chloride, a mixture of sodium chloride and mineral salts, or the like: solutions of mannitol, lactose, dextran, glucose, or the like: amino acid solutions of glycine, arginine, or the like: and mixed solutions having glucose solution with an organic acid solution or salt solution. Alternatively, these bases can also be prepared into injectable agents in the form of a solution, suspension, or dispersion, with use of auxiliary agents such as an osmoregulator, a pH adjuster, a vegetable oil, and a surfactant, in accordance with usual methods which are already known to those skilled in the art. These injectable agents can also be prepared in the form of a pharmaceutical preparation to be dissolved at the time of use, through operations such as powderization or lyophilization.

The form of administration of the loss-of-function allele may be either systemic administration such as usual intravenous administration and intraarterial administration, or local administration such as local injection and oral administration. Furthermore, administration may also take a combined form with catheterization, gene introduction technology, or surgical operation.

The administration dose of the loss-of-function type gene varies depending on the age and gender of the patient, the symptom, the administration route, the frequency of administration, and the dosage form. Generally, the daily dose for an adult is within a range of about 1 µg/kg of body weight to 1000 mg/kg of body weight, and preferably a range of about 10 µg/kg of body weight to 100 mg/kg of body weight, in terms of weight of recombinant gene. The frequency of administration is not particularly limited.

Moreover, the abovementioned various gene therapeutic agents of the present invention can also be produced by adding a gene into a suspension of liposomes prepared by a usual method, followed by freezing and subsequent thawing. Examples of the method for preparing liposomes include a membrane shaking method, a sonication method, a reverse phase evaporation method, and a surfactant removal method. The suspension of liposomes is preferably subjected to sonication treatment before addition of a gene, so as to improve the efficiency of encapsulation of the gene. The liposomes having the gene encapsulated therein may be intravenously administered either directly or in the form of a suspension with water, physiological salt solution, or the like.

The cell growth suppressing agent of the present invention is useful as an anti-tumor agent. The term "anti-tumor" used herein has its broadest meaning which includes both of a preventive function of preventing generation, metastasis or implantation of tumor and a therapeutic function of suppressing the growth of tumor cells, regressing tumor to inhibit progress of tumor or improving the symptom. The term "anti-tumor" is not interpreted in a limited way.

Specific examples of cancer to be treated with the antitumor agent of the present invention include, but are not limited to, malignant melanoma, malignant lymphoma, lung cancer, esophageal cancer, gastric cancer, large bowel cancer, rectal cancer, colonic cancer, ureteral tumor, gallbladder cancer, bile duct cancer, biliary tract cancer, mammary cancer, liver cancer, pancreatic cancer, testicular tumor, maxillary cancer, lingual cancer, labial cancer, oral cavity cancer, pharyngeal cancer, laryngeal cancer, ovarian cancer, uterine cancer, prostate cancer, thyroid gland cancer, brain tumor, Kaposi's sarcoma, angioma, leukemia, polycythemia vera, neuroblastoma, retinoblastoma, myeloma, bladder tumor, sarcoma, osteosarcoma, myosarcoma, skin cancer, basal cell cancer, skin appendage carcinoma, metastatic skin cancer, and cutaneous melanoma. Preferably, the cancer is esophageal cancer.

(3) Method for Detection of Tumor Using SMYD2 Gene

The detection method for selecting target tumor, to which the cell growth suppressing agent (antitumor agent) of the present invention can be applied, comprises a step of analyzing SMYD2 gene in a specimen, using DNA or RNA comprising the entire or a part of the SMYD2 gene. The term "a part of the SMYD2 gene" is used herein to mean an oligonucleotide consisting of, for example, approximately 10 to 30 contiguous nucleotides in the nucleotide sequence of the SMYD2 gene. As a specimen, there can be used a tissue section, blood, lymph, sputum, lung wash solution, urine, feces, tissue culture supernatant, or the like, which are suspected to comprise tumor cells.

The aforementioned expression such as "detection for selecting target tumor to which the cell growth suppressing agent (antitumor agent) can be applied" is used to mean examination of the presence or absence of tumor in tissues or the like, on which the cell growth suppressing agent (antitumor agent) of the present invention effectively acts.

The detection for selecting tumor is carried out by analyzing SMYD2 gene in a specimen, using DNA or RNA comprising the entire or a part of the SMYD2 gene as a primer or a probe. The term "to analyze SMYD2 gene" is used herein to specifically mean detection of amplification or deletion of the SMYD2 gene in genomic DNA, or detection of the abnormality of the expression level of the gene.

In the case of using the aforementioned DNA or RNA as a primer, mutation of the gene can be detected, for example, by amplifying a partial sequence of DNA prepared from a specimen according to a PCR method using two types of selected primers and then confirming the presence thereof, or by confirming the sequence of an amplification product or the sequence of an amplification product that has been incorporated into various types of plasmid vectors.

On the other hand, the abnormality of the expression level of the gene can be detected by a Northern hybridization method or an RT-PCR (reverse transcription-polymerase chain reaction) method using a probe comprising the aforementioned RNA sequence.

(4) Detection Method for Selecting Tumor Using Antibody Against SMYD2 Protein, or Fragment Thereof.

A detection method for selecting target tumor, to which the cell growth suppressing agent (antitumor agent) of the present invention can be applied, comprises a step of analyzing the amount of SMYD2 protein contained in a specimen, using an antibody against the SMYD2 protein, or a fragment of said antibody.

An antibody against the SMYD2 protein used in the present invention (hereinafter referred to as an "SMYD2 antibody") can be produced by an ordinary method using the entire or a part of SMYD2 protein as an antigen. A part of SMYD2 protein means a polypeptide consisting of, for example, at least 6, preferably at least approximately 8 to 10, and more preferably at least approximately 11 to 20 contiguous amino acids in the amino acid sequence of the SMYD2 protein as shown in SEQ ID NO: 2. As a method of preparing the entire or a part of SMYD2 protein used as an antigen, either a biological method or a chemical synthesis method may be applied.

A polyclonal antibody can be produced, for example, by sufficiently immunizing an animal such as a mouse, a guinea pig, or a rabbit with the aforementioned antigen via inoculating the antigen into the subcutis, muscle, abdominal cavity, vein, or the like of such animal several times, and then collecting blood from such animal, followed by separation of serum. A monoclonal antibody can be produced, for example, by preparing hybridomas via cell fusion between the splenic cells of the mouse immunized with the aforementioned antigen and commercially available mouse myeloma cells, and then producing the monoclonal antibody from a culture supernatant of the hybridomas or from the ascites fluid of the mouse to which the hybridomas have been applied.

Using the thus prepared antibody against SMYD2 protein or a fragment thereof, the expression level of an SMYD2 protein contained in a specimen can be measured. For such measurement, immunological methods such as immunoblotting, enzyme immunoassay (EIA), radioimmunoassay (RIA), a fluorescence antibody method or immunocytostaining, or a Western blotting method may be applied, for example. Herein, a fragment of the antibody against SMYD2 protein means a single chain antibody fragment (scFv) of the antibody, etc. In addition, as a specimen, there can be used a bone marrow sample, a tissue section, blood, lymph, sputum, lung wash solution, urine, feces, tissue culture supernatant, or the like, which are suspected to comprise tumor cells. When the thus measured expression level of the SMYD2 protein in the specimen is low, expression of the SMYD2 gene is suppressed in tissues or cells used as specimens, and thus a target tumor, to which the antitumor agent of the present invention can be applied, can be selected.

The present invention is hereafter described in greater detail with reference to the following examples, although the technical scope of the present invention is not limited to these examples.

EXAMPLES

Experimental Materials

Forty three (43) types of ESCC cell line (Table 1) used herein were established from clinical samples. These cell lines were cultured using 10% fetal calf serum and a 100 U/ml penicillin/100 μg/ml streptomycin solution.

TABLE 1

Panel of esophageal squamous cell carcinoma cell lines used in this study
Cell line name KYSE30
KYSE70
KYSE110
KYSE140
KYSE150
KYSE170
KYSE180
KYSE190
KYSE200
KYSE220
KYSE270
KYSE350
KYSE410
KYSE450
KYSE510
KYSE520
KYSE590
KYSE770
KYSE790
KYSE850
KYSE890
KYSE960
KYSE1170
KYSE1190
KYSE1240
KYSE1250
KYSE1260
KYSE1440
KYSE2270
KYSE2400
KYSE2650
TE1
TE2
TE4
TE5
TE6
TE8
TE9
TE10
TE11
TE13
TE14
TE15

Also, specimens from 153 cases of surgical patients with esophageal carcinoma were analyzed by immunohistostaining. Clinical specimens used herein were fixed samples of consecutively admitted patients who had received esophagectomy between 1981 and 2005 at the Department of Surgery, National Defense Medical College Hospital. Regarding the use of clinical specimens, we have explained the relevant content in the format as specified by the ethical committees of the relevant organizations and received consent in writing from patients. None of the cases analyzed herein had been subjected to presurgical treatment such as demucosation, chemotherapy, or radiation therapy.

Example 1

Amplicon Mapping for the 1q32-1q41 Gene Region in ESCC Cell Lines

For detection of new genetic changes in esophageal carcinoma, an approximately 12-MB amplification region located at 1q32-1q41 (among known amplification regions of ESCC cell lines disclosed in the CGH data base Japan (http://www.cghtmd.jp/CGHDatabase/)) was mapped by high-density oligo array (Agilent 244 K high-density oligo-array) CGH analysis and the FISH method using genomic DNAs prepared from the above 43 types of ESCC cell line. Thus, 42 candidate genes within the region were identified (FIG. 1A). Specifically, in the region with the highest number of copies among slight changes in the number of copies as evaluated using the oligo array, an HSR (Homogeneously Staining Region) pattern was detected in the regions ranging from circled number 1 to circled number 4 even by the FISH method. In BAC regions with circled number 6 and circled number 8, changes in signal pattern in correlation with decreases in the number of copies were observed (FIG. 1B). Also, the region at a step higher than the other was found to contain 22 types of gene (FIG. 1A).

In addition, as a control, genome extracted from esophagus-derived normal cells was labeled with Cy5. As DNAs to be tested, genomic DNAs prepared from ESCC cancer cell lines were labeled with Cy3.

A specific analytical method for Agilent 244K high-density oligo-array CGH analysis is as described below. This is a direct method not involving amplification of genomic DNA.

1. Restriction Enzyme Reaction of Genomic DNA

DNA (2 μg) was diluted with nuclease free water and then each sample was adjusted to be a total of 20.2 μl. Next, 2.0 μl of nuclease-free water, 2.6 μl of 10× reaction buffer C, 0.2 μl of acetylated BSA (10 μg/μl), 0.5 μl of Alu I (10 U/μl), and 0.5 μl of Rsa I (10 U/μl) were added per reaction, so that a total of 26 μl of a solution was prepared. The resultants were incubated for 2 hours with a water bath at 37° C. or a heat block. After completion of the reaction, the resultants were incubated for 20 minutes with a heat block at 65° C., so as to inactivate the enzymes. After inactivation, the resultants were placed on ice.

2. Labeling of Genomic DNA

Restriction enzyme-digested genomic DNAs were labeled using an Agilent Genomic DNA Labeling kit. Specifically, Cyanine-3-dUTP or Cyanine-5-dUTP was incorporated by a reaction using random primers and Exo-Klenow, so that genomic DNAs were labeled.

3. Purification and Measurement of Labeled DNA

Labeled DNAs were purified and concentrated using Microcorn YM-30 filter units (Millipore, Product No. 42410). Labeled DNAs were measured using NanoDrop ND-1000 (UV-Vis spectrophotometer). Efficiencies of incorporating Cy3-dUTP and Cy5-dUTP were calculated.

4. Hybridization

A solution (153 μl) of a labeled sample (mixture of Cy3- and Cy5-labeled DNAs), 50 μl of Human Cot-1 DNA (1.0 mg/ml), 52 μl of 10×Blocking Agent, and 260 μl of 2× Hybridization Buffer were added, followed by 3 minutes of incubation at 95° C. and then 30 minutes of incubation at 37° C. An array slide was set within a hybridization chamber and then the solution was applied thereto. Hybridization was carried out for 40 hours using a rotor of an oven at 65° C.

5. Washing of Slide Glass and Scanning

Washing was carried out with Agilent Oligo aCGH washing buffer 1 and Agilent Oligo aCGH washing buffer 2, and then scanning was carried out using an Agilent scanner. Scanning images were quantified using Agilent Feature Extraction software, and then changes in the number of copies were visualized and expressed using CGH analysis software.

Also, FISH analysis was specifically conducted by a standard method (Inoue J, Otsuki T, Hirasawa A, et al. Am J. Pathol.; 165: 71-81., 2004) using probe sets listed in Table 2 and the BAC (RP11-82D16) 1q36.3 region or the BAC (RP11-351H16) 1p42 region as a control probe.

TABLE 2

42 target genes and the positions in the 1q32-41 amplification region

| ProbeName | ChrName | Start | Stop | Name of Gene |
|---|---|---|---|---|
| A_16_P00030448 | chr1 | 24051059 | 24051118 | FUSIP1 |
| A_16_P35209254 | chr1 | 86112979 | 86113038 | COL24A1 |
| A_14_P121334 | chr1 | 173983060 | 173983119 | FAM5B |
| A_14_P131903 | chr1 | 208502918 | 208502973 | BC009918 |
| A_16_P00247914 | chr1 | 208595874 | 208595933 | INTS7 |
| A_14_P108506 | chr1 | 208666099 | 208666158 | DTL |
| A_14_P126109 | chr1 | 208890958 | 208891017 | PPP2R5A |
| A_16_P00248345 | chr1 | 208936937 | 208936996 | C1orf75 |
| A_14_P137805 | chr1 | 208996575 | 208996634 | NENF |
| A_16_P00248524 | chr1 | 209072811 | 209072870 | BC028700 |
| A_16_P15438150 | chr1 | 209173039 | 209173098 | ATF3 |
| A_14_P200051 | chr1 | 209187361 | 209187412 | FAM71A |
| A_14_P101656 | chr1 | 209256216 | 209256275 | SNFT |
| A_16_P35457045 | chr1 | 209289206 | 209289265 | AK124596 |
| A_14_P137130 | chr1 | 209352154 | 209352213 | C1orf48 |
| A_16_P15438607 | chr1 | 209377782 | 209377841 | AL832248 |
| A_16_P15438607 | chr1 | 209377782 | 209377841 | AL832248 |
| A_16_P35457267 | chr1 | 209397863 | 209397922 | LOC149643 |
| A_16_P15438672 | chr1 | 209415513 | 209415572 | AK092887 |
| A_16_P15438719 | chr1 | 209434384 | 209434443 | FLVCR |
| A_14_P130306 | chr1 | 209458019 | 209458078 | AK001419 |
| A_16_P15438922 | chr1 | 209536347 | 209536405 | FLJ12505 |
| A_16_P35457650 | chr1 | 209562108 | 209562167 | ANGEL2 |
| A_16_P35457771 | chr1 | 209627210 | 209627269 | RPS6KC1 |
| A_16_P00250390 | chr1 | 210395603 | 210395662 | AK092251 |
| A_14_P132471 | chr1 | 210550049 | 210550099 | U44060 |
| A_16_P00250786 | chr1 | 210591141 | 210591200 | PROX1 |
| A_16_P00251236 | chr1 | 210868316 | 210868375 | SMYD2 |
| A_16_P15443000 | chr1 | 211088071 | 211088130 | PTPN14 |
| A_14_P135064 | chr1 | 211215490 | 211215549 | CENPF |
| A_16_P15444629 | chr1 | 211768498 | 211768557 | KCNK2 |
| A_14_P127442 | chr1 | 212183435 | 212183494 | KCTD3 |
| A_16_P15447415 | chr1 | 212865824 | 212865923 | USH2A |
| A_14_P110748 | chr1 | 213066274 | 213066333 | ESRRG |
| A_16_P15450746 | chr1 | 214082257 | 214082316 | GPATC2 |
| A_14_P135206 | chr1 | 214363493 | 214363552 | SPATA17 |
| A_16_P15451754 | chr1 | 214460705 | 214460764 | BC040896 |
| A_14_P109765 | chr1 | 214611903 | 214611962 | BC039113 |
| A_16_P15452702 | chr1 | 214855791 | 214855850 | CGI-115 |
| A_14_P114581 | chr1 | 214975773 | 214975832 | TGFB2 |
| A_16_P15454704 | chr1 | 215649847 | 215649906 | BC086863 |
| A_16_P00258940 | chr1 | 215754831 | 215754890 | LYPLAL1 |
| A_16_P35475530 | chr1 | 216435355 | 216435414 | AK097467 |
| A_16_P00260014 | chr1 | 216488831 | 216488890 | SLC30A10 |
| A_16_P15456820 | chr1 | 216519741 | 216519800 | AK097467 |
| A_16_P35475827 | chr1 | 216545930 | 216545989 | EPRS |
| A_16_P15457113 | chr1 | 216631079 | 216631138 | BPNT1 |
| A_16_P00260323 | chr1 | 216701905 | 216701964 | IARS2 |
| A_16_P15457571 | chr1 | 216814005 | 216814064 | RAB3GAP2 |
| A_16_P15458454 | chr1 | 217176641 | 217176700 | MARK1 |
| A_14_P135863 | chr1 | 217258565 | 217258624 | C1orf115 |
| A_14_P115271 | chr1 | 217336800 | 217336859 | MOSC2 |
| A_14_P131287 | chr1 | 217346415 | 217346474 | BC010366 |
| A_16_P00261300 | chr1 | 217365187 | 217365246 | MOSC1 |
| A_14_P108178 | chr1 | 217446670 | 217446716 | HLX1 |
| A_14_P126288 | chr1 | 218263439 | 218263498 | DUSP10 |
| A_16_P15462025 | chr1 | 218676736 | 218676795 | BC023608 |
| A_14_P115492 | chr1 | 219238579 | 219238638 | C1orf80 |
| A_16_P15463513 | chr1 | 219300768 | 219300827 | FLJ43505 |
| A_14_P127398 | chr1 | 219503635 | 219503694 | DISP1 |
| A_16_P00263233 | chr1 | 219892814 | 219892873 | SUSD4 |
| A_14_P133449 | chr1 | 219940496 | 219940555 | C1orf65 |

TABLE 2-continued 42 target genes and the positions in the 1q32-41 amplification region

| ProbeName | ChrName | Start | Stop | Name of Gene |
|---|---|---|---|---|
| A_16_P15465520 | chr1 | 220228115 | 220228174 | CAPN2 |
| A_16_P00263725 | chr1 | 220301344 | 220301403 | TP53BP2 |
| A_16_P15466482 | chr1 | 220640889 | 220640948 | FBXO28 |
| A_16_P00289255 | chr1 | 238796201 | 238796260 | PLD5 |

Example 2

Quantitative Analysis Regarding mRNA Expression of the Above 22 Genes

With use of the above 43 ESCC cell lines, quantitative analysis was conducted regarding mRNA expression of 22 types of gene selected in Example 1. An epithelium of a normal esophagus was used to represent a control expression level in quantitative RT-PCR. Total RNA was collected from each cell at the logarithmic growth phase and then cDNA was constructed by a standard method. cDNA was subjected to measurement of mRNA expression level by a quantitative real-time fluorescence detection method (ABI PRISM 7500 sequence detection System; Applied Biosystems, Foster City, Calif., U.S.A.) using protocols of TaqMan Gene Expression Assays (ABI, Applied Biosystems) and primers specific to each gene.

Figure 2:
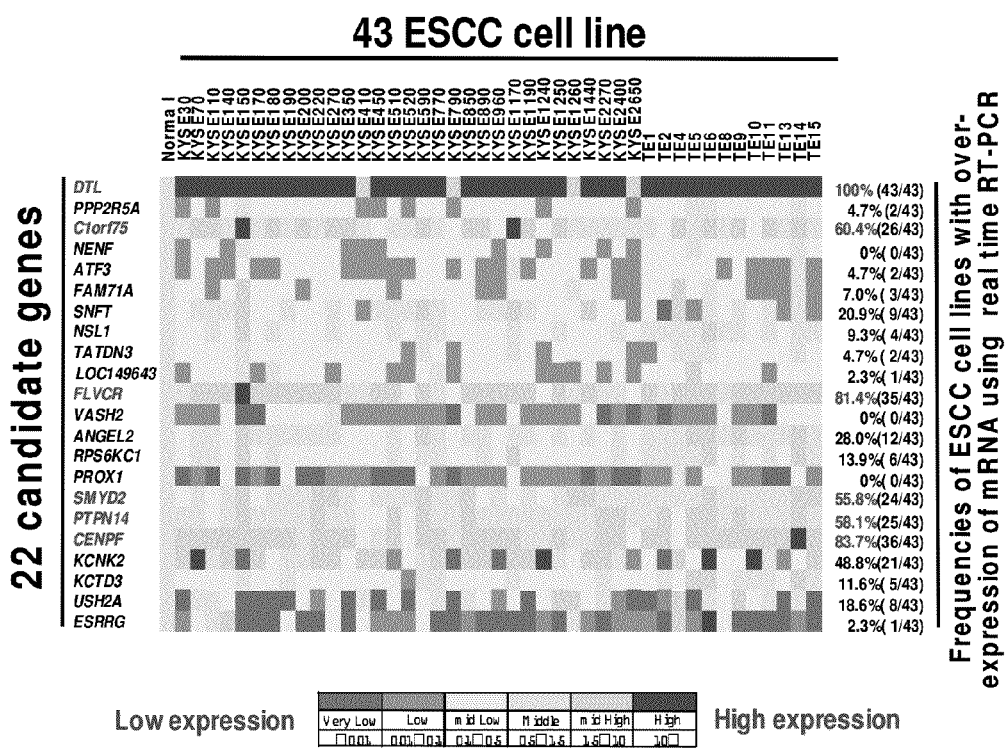
FIG. 2 shows the expression patterns of 22 genes. The longitudinal axis on the left indicates the names of 22 types of gene, the horizontal axis indicates the names of 43 types of cell line used for analysis, and the longitudinal axis on the right indicates the percentages of cell lines exerting expression at levels higher than those of normal esophageal tissues. A table in the lower column shows the correlation between the degrees of expression and colors used for filling.

FIG. 2 shows the results. In FIG. 2, gene names are shown on the left, cell line names are shown on the top, and frequencies of cell lines exhibiting high-level expression in the normal tissues are shown on the right. Based on these results and various databases (NCBI, LSBM, and others), genes found to be expressed at high levels and high frequencies in 43 ESCC cell lines and to tend to be more frequently expressed in cancer cell lines than in normal tissues even in the case of other types of carcinoma as revealed by LSBM were focused. As a result, 10 candidate genes: that is, DTL, C1orf75, ATF3, SNFT, NSL1, FLVCR, ANGEL2, SMYD2, PTPN14, and CENPF genes, were found to have the characteristics (FIG. 2).

Example 3

Knockdown Experiment Using siRNA of the Above 10 Genes

Knockdown was carried out using various siRNAs of the 10 types of gene in Example 2 and then cell growth assay was carried out. Specifically, amplification cell lines were subjected to analysis using an siRNA of Santa Cruzs (Santa Cruz Biotechnology, Inc.), Dharmacon (Lafayette, Colo., USA), or Sigma (Tokyo, Japan). Transfection was carried out using Lipofectamine 2000 (Invitrogen, St. Louis, Mo., U.S.A.) in reference to the protocols attached to siRNA (Santa Cruzs 10 nmol/L, Dharmacon 20 nmol/L, or Sigma 50 nmol/L). The degree of suppression of growth was evaluated using WST assay (colorimetric water-soluble tetrazolium salt assay).

Figure 3:
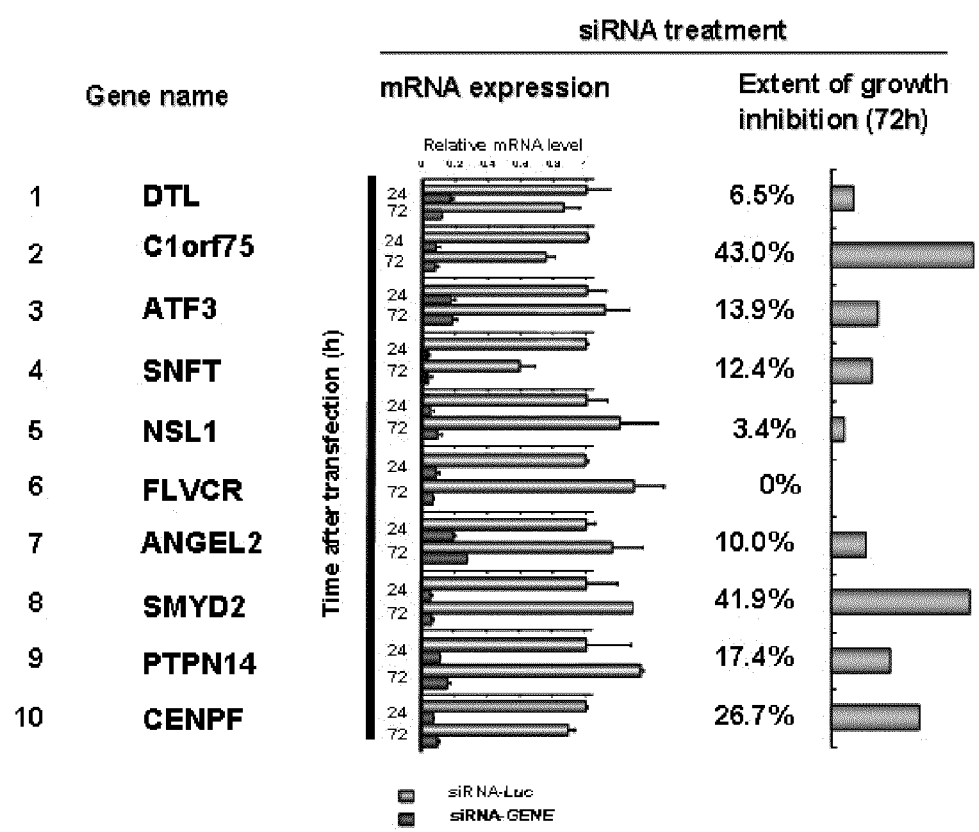
FIG. 3 shows the effects of suppressing mRNA expression by siRNAs corresponding to the 10 types of gene of the present invention. Ten (10) types of candidate gene name are shown on the left, the results of confirming knockdown at the mRNA level using siRNAs of the 10 types of gene are shown on the center, and the degrees of mRNA suppression at 72 hours after knockdown treatment are shown on the right.

FIG. 3 shows the results. The mRNA expression levels were shown on the right in FIG. 3. Knockdown by siRNAs was confirmed by quantitative analysis conducted for expression. Particularly C1orf75 and SMYD2 were found to exert significant effects of suppressing growth at 72 hours (FIG. 3).

Example 4

Confirmation of Amplification of SMYD2 Gene by FISH Method

For confirmation of amplification of the SMYD2 gene, BAC RP11-74E6 (1q41 and SMYD2; green) was analyzed by the FISH method using RP11-82D16 (1p36.3, control; red) as a control. Analysis was conducted by a standard method (Inoue J, Otsuki T, Hirasawa A, et al., Am J Pathol; 165: 71-81., 2004).

Figure 4:
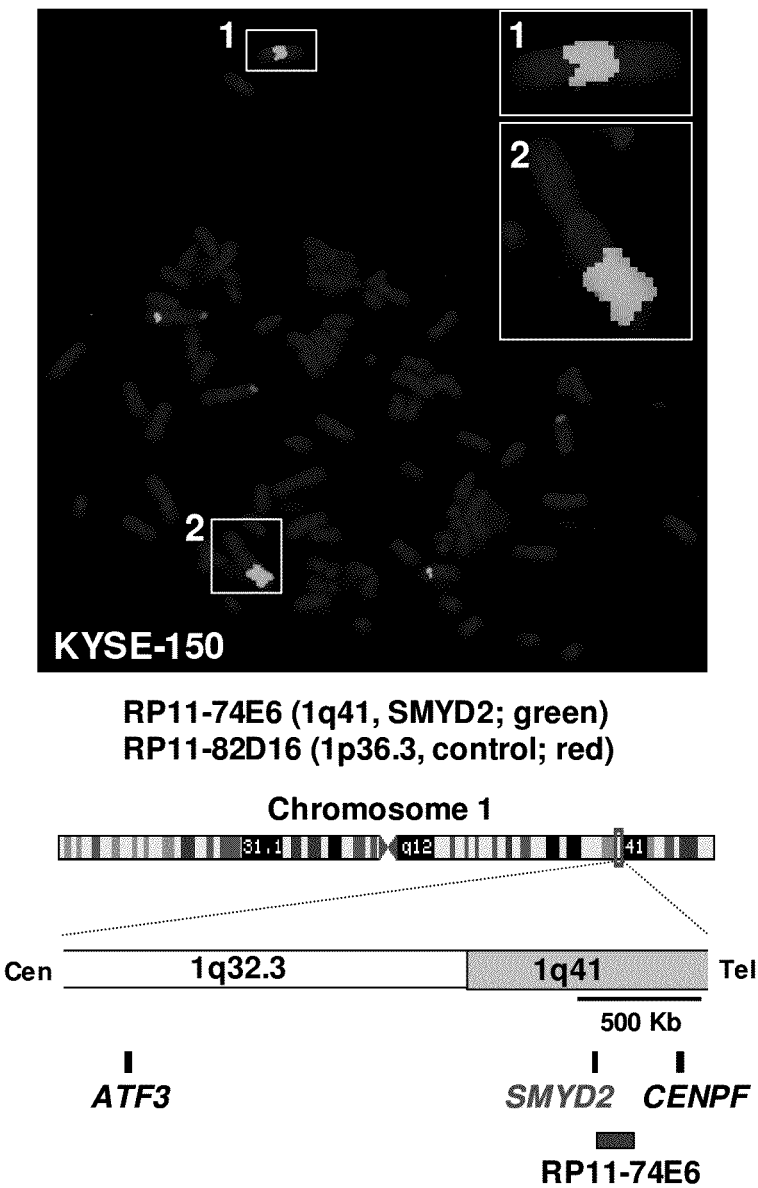
FIG. 4 shows the results of FISH analysis regarding a KYSE cell line (middle phase). Green indicates fluorescence signal from RP11-74E6 (containing 1q41 and SMYD2) and red indicates the fluorescence signal from a control (1p36.3).

FIG. 4 shows the results. Formation of the HSR (Homogeneously Staining region) pattern was confirmed.

Example 5

Quantitative Analysis Regarding Expression of Esophageal Carcinoma Cell Line Expressing SMYD2 mRNA For confirmation of enhanced expression of the SMYD2 gene at the mRNA level, quantitative expression analysis (real-time RT-PCR) was conducted for 43 ESCC cell lines. cDNA was subjected to measurement of mRNA expression levels by a quantitative real-time fluorescence detection method (ABI PRISM 7500 sequence detection System; Applied Biosystems, Foster City, Calif., U.S.A.) using the protocols of TaqMan Gene Expression Assays (ABI, Applied Biosystems) and primers specific to the SMYD2 gene.

Figure 5:
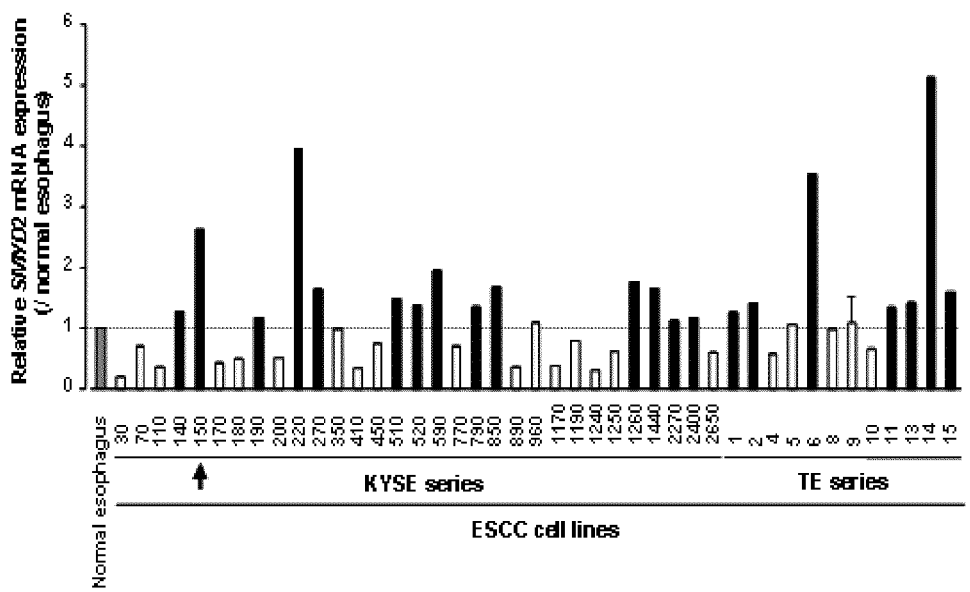
FIG. 5 shows the results of quantitative expression analysis regarding SMYD2 in 43 ESCC cell lines using the Real-time RT-PCR method.

FIG. 5 shows the results. As shown in FIG. 5, 55.8% (24/43) of the ESCC cell lines were observed to undergo high-level expression from the tissues of normal esophageal mucosa.

Example 6

Confirmation of Protein Expression Level of SMYD2 Gene

Figure 13:
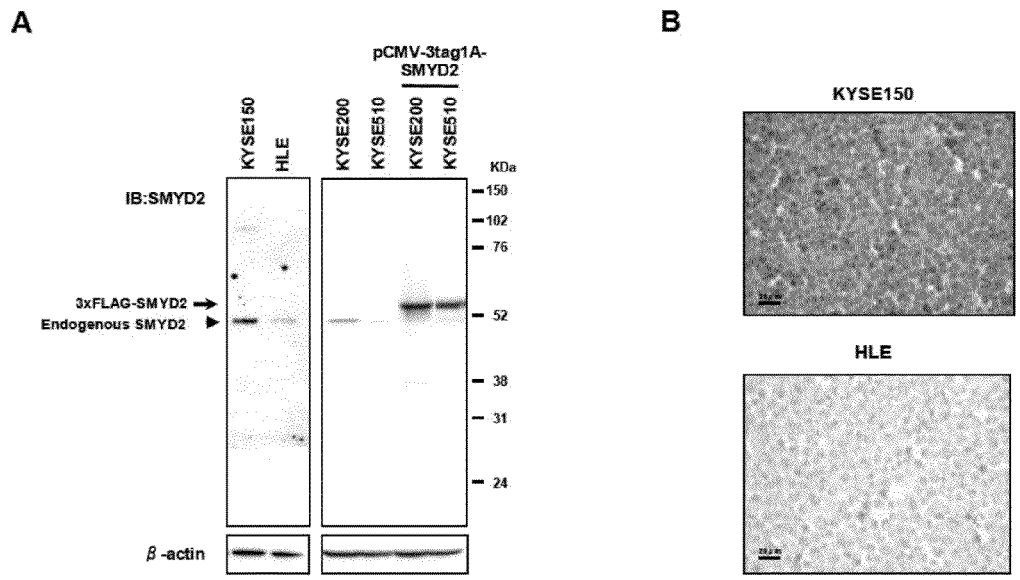
FIG. 13 shows the accuracy evaluation for the prepared SNYD2-specific antibody.

For confirmation of SMYD2 gene overexpression in ESCC cell lines, protein expression was analyzed by the Western blot method using a specific antibody. Specifically, cells of each cell line were dissolved in RIPA buffer (10 mM Tris-HCl, 150 mM NaCl, 1 mM EDTA, 1% sodium deoxycholate, 0.1% SDS, 1% Triton X-100, pH7.4) containing a protease-inhibitor cocktail (Roche Diagnostics). Protein concentrations were then measured by BCA assay (Pierce Chemical) and then 20 µg each thereof was subjected to SDS-polyacrylamide gel electrophoresis. The resultants were transferred to difluoride membranes. The specific antibody used herein was prepared by preparing an anti-SMYD2 polyclonal antibody (HPYISEIKQEIESH (SEQ ID NO: 5); Operon Biotechnology, Tokyo, Japan) with the use of a peptide comprising 12 amino acids of human SMYD2 and then carrying out affinity purification. SMYD2 antibody assay was carried out using a KYSE150 cell line as a positive control and HLE or KYSE510 as a negative control. Confirmation was also carried out by causing KYSE200 and KYSE510 to undergo overexpression of pCMV-3tag1A-SMYD2 and then detecting using a FLAG tag antibody or a SMYD2 antibody (FIG. 13). After primary detection using an anti-β-actin antibody (Sigma) as a control, color development and detection were carried out using a peroxidase-conjugated secondary antibody and an enhanced electrochemiluminescence system (Amersham).

Figure 6:
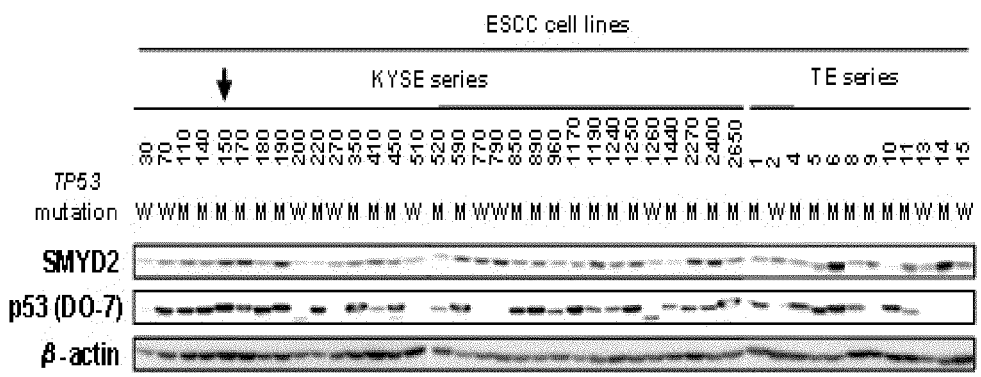
FIG. 6 shows the results of analyzing SMYD2 and p53 protein expression in 43 ESCC cell lines by the Western blot method. The first row shows the result of the SMYD2 protein, the second row shows the result of the p53 protein, and the third row shows the result of β-actin as a control.

FIG. 6 shows the results. As shown in FIG. 6, highly frequent expression was confirmed almost in correlation with mRNA expression.

Example 7

Confirmation of Growth-Suppressing Effects of ESCC Cells by WST Assay (Colorimetric Water-Soluble Tetrazolium Salt Assay)

For examination of the effects of SMYD2 overexpression on ESCC cell growth, analysis was conducted by WST assay (colorimetric water-soluble tetrazolium salt assay). A specific experimental method is as follows.

Decreases in the mRNA expression levels were analyzed by a method similar to that in Example 3. An siRNA corresponding to the SMYD2 gene was designed as being GCAAAGAUCAUCCAUAUAUUU (SEQ ID NO: 3) and purchased (Sigma). Also, as a control siRNA, CGUACGCGGAAUACUUCGAUU (SEQ ID NO: 4) corresponding to a luciferase gene was purchased (Sigma). Each synthesized siRNA (10 nmol/L) was transferred into each ESCC cell line using a Lipofectamine siRNA MAX reagent (Invitrogen Corporation) (treated according to protocols for the product).

Figure 7:
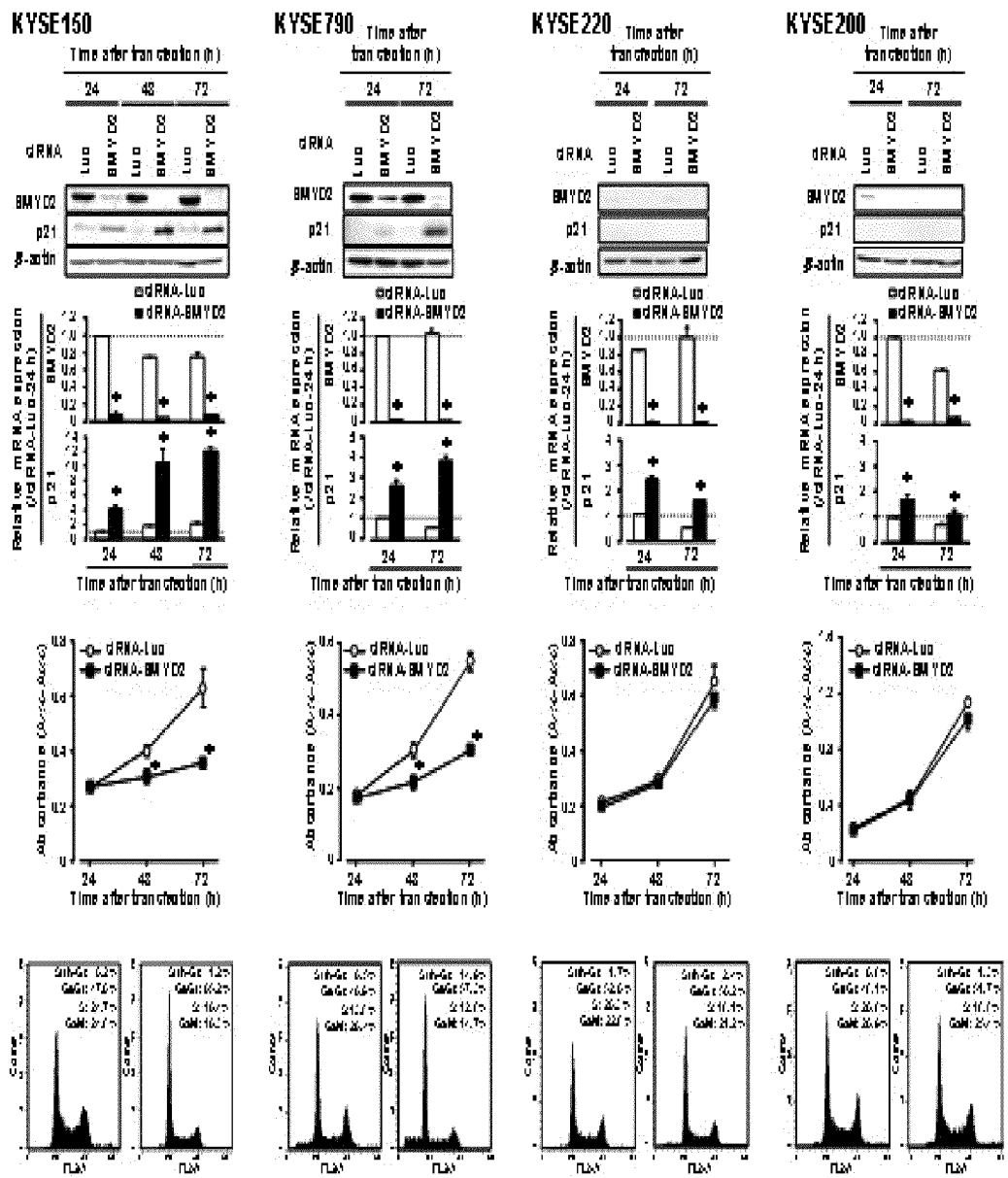
FIG. 7 shows the results of cell growth analysis using SMYD2. Regarding KYSE150 (high-level expression of SMYD2, p53 mutation (+)), KYSE790 (high-level expression of SMYD2, p53 wild type), KYSE220 (low-level expression of SMYD2, p53 mutation (+)), and KYSE200 (low-level expression of SMYD2, p53 wild type), the upper column shows the results of Western blot analysis involving knockdown using si-RNA, the upper middle column shows changes in mRNA expression level using quantitative RT-PCR, the lower middle column shows the result of analysis using MTT assay, and the bottom column shows the result of FACS analysis after 72 hours.

FIG. 7 shows the results. It was confirmed by the RT-PCR method that SMYD2 mRNA expression was more significantly suppressed in cells (containing amplified and/or overexpressed SMYD2) after 24 to 72 hours by an SMYD2-specific siRNA than a non-specific control siRNA. It was also confirmed by the Western blot method that endogenous SMYD2 protein expression was suppressed. An anti-β-actin antibody was used as a control. Furthermore, SMYD2 expression was suppressed by a specific siRNA and then WST assay and FACS analysis were conducted. As a result of knockdown for KYSE150 and KYSE790 cell lines expressing SMYD2 at high levels, 40% or more effects of suppressing cell growth was confirmed by 72 hours of WST assay after transfection and G1-S arrest was confirmed by the FACS analysis. It was also confirmed at this time by the RT-PCR method and the Western blot method that p21 expression was induced. Among 43 ESCC cell lines, KYSE220 and KYSE200 cell lines expressing SMYD2 at extremely low protein levels were similarly subjected to knockdown using an siRNA and then the effects of suppressing growth were compared. Almost no effects of suppressing growth (due to SMYD2 knockdown) were observed in the cell lines expressing SMYD2 at low levels. No G1-S arrest was confirmed by FACS analysis and induction of p21 expression was never confirmed by the RT-PCR method and the Western blot method. Confirmation was carried out for these cell lines not only by the WST assay but also by the real-time RT-PCR and the Western blot method. As described above, the effects of suppressing growth (oncogene addiction) were observed depending on the SMYD2 protein expression levels. It was thus revealed that an SMYD2 target molecule used for treatment had low effects on normal tissues expressing SMYD2 at low levels, so that the degree of adverse reaction could be lowered. As described above, the effects of suppressing growth were confirmed more significantly in the KYSE150 cell line (in which SMYD2 had been amplified) subjected to SMYD2 knockdown compared with the control at the RNA level and the protein level and in terms of macroscopic findings concerning cell amplification (FIG. 7).

Example 8

Analysis of Mode of Action of SMYD2 Gene Using Fluorescence-Activated Cell Sorting (FACS) Method For revealing the mode of action of SMYD2 with respect to the cell cycle of ESCC cells, the cell cycle of cells in which an SMYD2-specific siRNA had been introduced was compared with that of control cells by FACS analysis with the use of KYSE150 and KYSE790 cell lines expressing SMYD2 at high levels and KYDE220 and KYSE200 cell lines expressing SMYD2 at low levels (FIG. 7).

Specifically, after trypsin treatment, cells were fixed overnight in a 70% ethanol solution, followed by 20 minutes of treatment with RNaseA (40 U/ml) and then 30 minutes of treatment with a PI solution (20 g/ml) of PBS buffer. The amount of DNA in cells was analyzed by a FACS Caliber cytometer and Cell Quest software (both produced by Becton-Dickinson). The experiment was carried out 3 times.

FIG. 7 shows the results. It was confirmed by the analysis that the cell lines expressing SMYD2 at high levels showed significantly increased fractional proportion of G0/G1, compared with the control, because of knockdown with siRNA-SMYD2. On the other hand, the cell lines expressing SMYD2 at low levels were found to show almost no difference with the control. It was revealed that SMYD2 activates the cell cycle at the G1/S check point, so as to be involved in cancer cell growth.

Example 9

Confirmation of the Presence or Absence of Activation of p53 Target Molecule by SMYD2 Gene Knockdown SMYD2 knockdown was carried out for esophageal squamous cell carcinoma cell lines by the method similar to that of Example 7, so as to confirm whether or not a p53 target molecule was activated.

Figure 9:
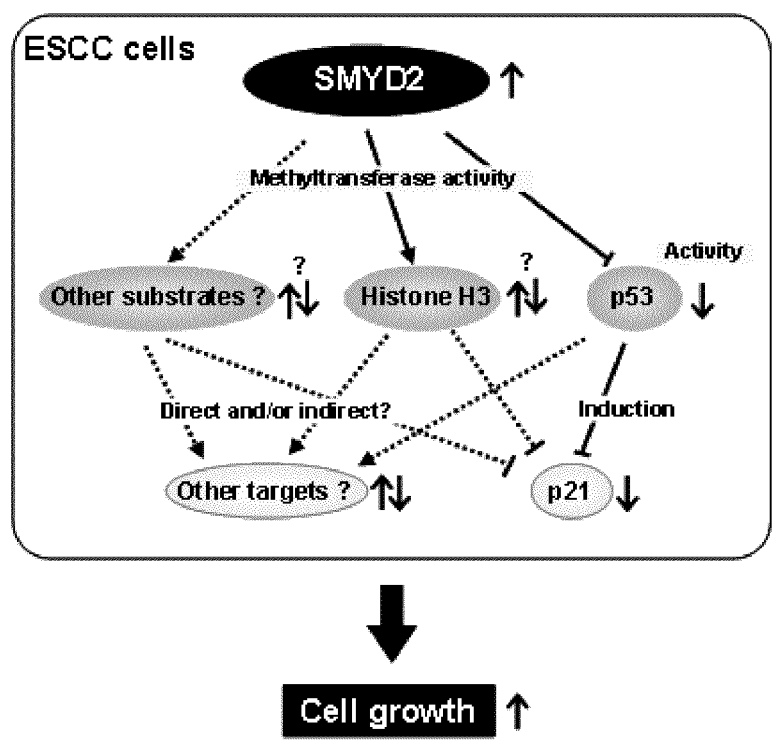
FIG. 9 shows the summary of SMYD2-associated molecules p53, p21, and Histone H3.
Figure 14:
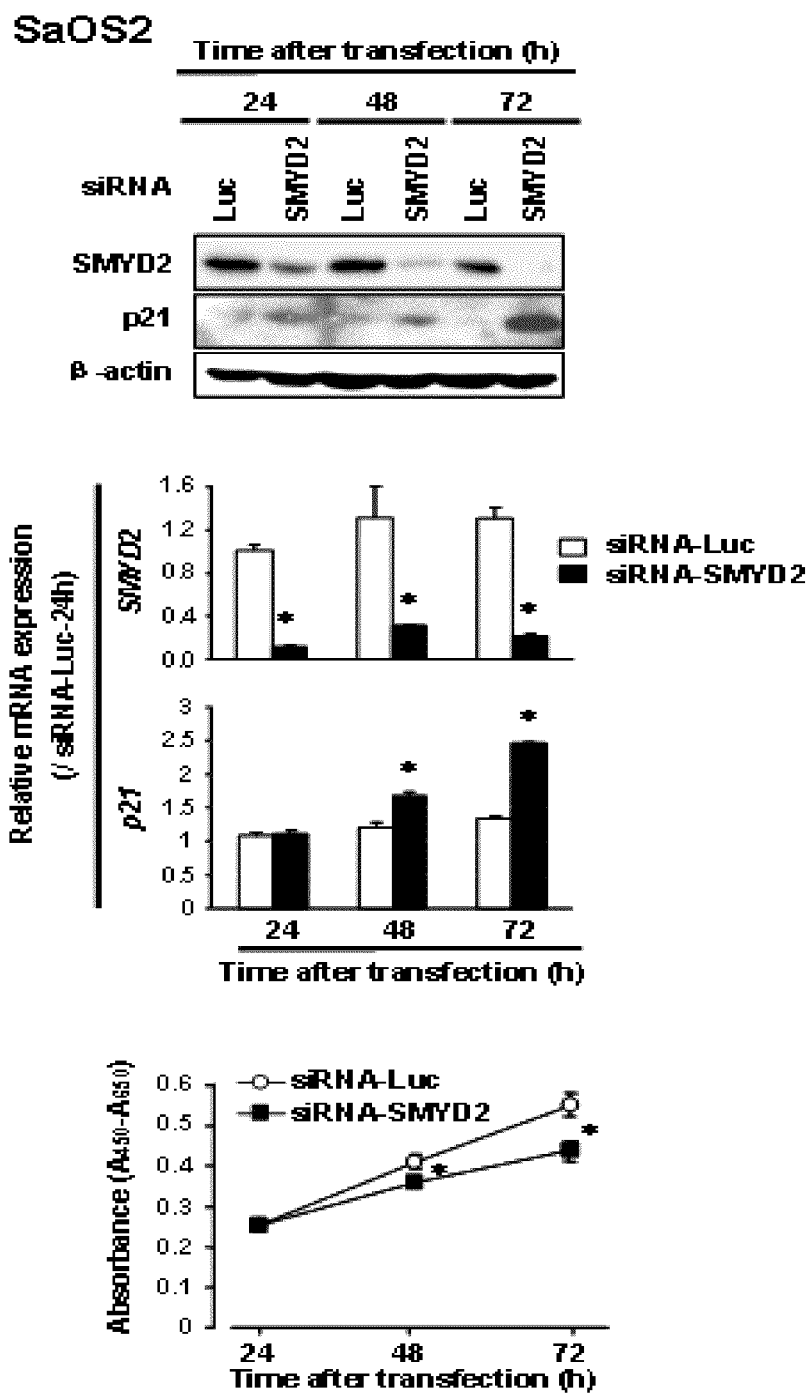
FIG. 14 shows that p21 expression was induced by SMYD2 knockdown in SaOS2 (p53 null cell line). This was confirmed at the mRNA (real-time Rt-PCR) level and the protein level (Western blotting). Slight effects of suppressing growth were observed by MTT assay.

As a result, it was revealed that p21, an index for cell-cycle arrest, was activated at the mRNA level. This was also similarly confirmed by the Western blot method. The results of FACS revealed that G1/S arrest was caused by induction of p21 (FIG. 7). Also, p21 expression induced by SMYD2 knockdown was also observed in the KYSE150 cell line expressing SMYD2 at a high level and having p53 mutation (+) and the SaOS2 (p53null) cell line. This revealed that p21 was induced not through mediation of p53, so as to cause the cell cycle to begin. It was demonstrated that SMYD2 is involved in cancer cell growth by suppressing partially p21 (independently of p21) to activate the cell cycle (FIG. 7, FIG. 9, and FIG. 14).

Example 10

Cell Growth Ability in SMYD2 Gene Overexpression System as Examined by Colony Formation Assay Cell growth ability in an SMYD2 gene overexpression system was examined by colony formation assay. Specifically, the KYSE200 and KYSE510 cell lines expressing SMYD2 at low levels were transfected with pCMV-3tag1A-empty, pCMV-3tag1A-SMYD2, and pCMV-3tag1A-SMYD2 MD (methylation defective mutant of SMYD2) vectors using lipofectamine 2000. Cells were collected after 24 hours and then protein expression from each plasmid vector was confirmed by the Western blot. At the same time, cells were plated at $1\times10^4$ cells/ml on petri dishes, selection was initiated 24 hours later with G418 (Neomycin), and then colony formation ability was evaluated.

Figure 8:
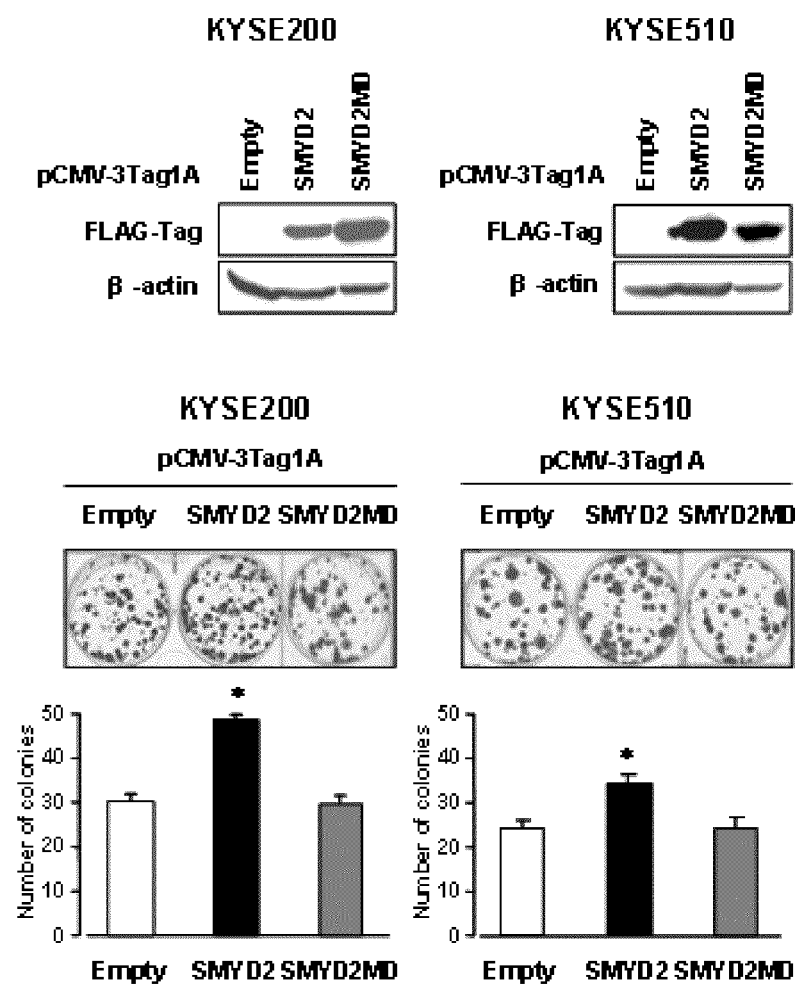
FIG. 8 shows the evaluation of cell growth ability in a SMYD2 gene overexpression system using colony formation assay. The result of the KYSE200 cell line is shown on the left and the result of the KYSE510 cell line is shown on the right. The top column shows proteins (obtained via transfection using pCMV-3tag1A-empty vector, pCMV-3tag1A-SMYD2, and pCMV-3tag1A-SMYD2 MD (methylation defective mutant of SMYD2) by Western blotting. The middle column shows photographs of colonies formed on petri dishes and the bottom column shows a graph showing the colony counts.

FIG. 8 shows the result for the KYSE200 cell line on the left and that for the KYSE510 cell line on the right. The top column shows proteins obtained via transfection with the pCMV-3tag1A-empty, pCMV-3tag1A-SMYD2, and pCMV-3tag1A-SMYD2 MD (methylation defective mutant of SMYD2) vectors as examined by Western blot. The middle column shows photographs of colonies formed on petri dishes. The bottom column shows a graph showing colony counts. When SMYD2 overexpression was caused, both KYSE200 and KYSE510 showed enhanced colony formation ability compared with that of the control. On the other hand, when an SMYD2 mutant was introduced, enhanced colony formation ability was never observed when compared with the control (FIG. 8).

Based on the above results, results of known reports are shown with black lines and contents deduced from the cell biological experimental data of Examples 1 to 10 are shown with black dotted lines, as summarized in FIG. 9.

Example 11

Figure 10:
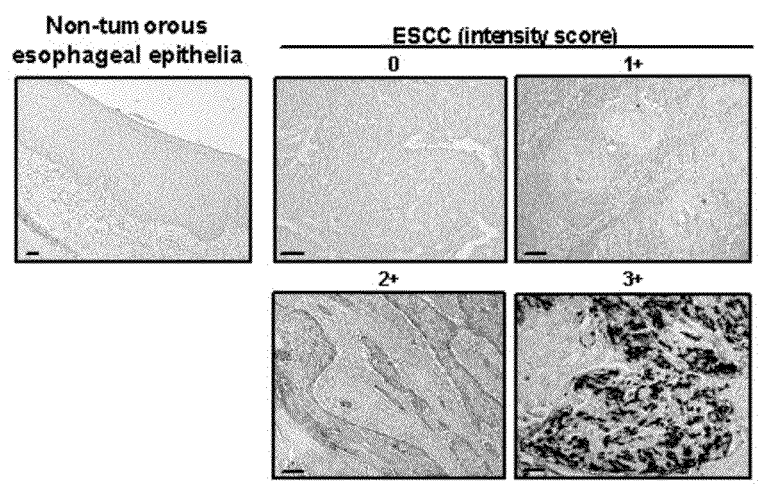
FIG. 10 shows the results of analyzing the expression levels of the SMYD2 protein by an immunohistochemical staining method. The upper column shows the staining conditions of SMYD2 as revealed by the immunohistochemical staining method using normal esophageal tissues. In the graph in the lower column, the horizontal axis indicates days elapsed after treatment and the longitudinal axis indicates survival rate.
Figure 10:
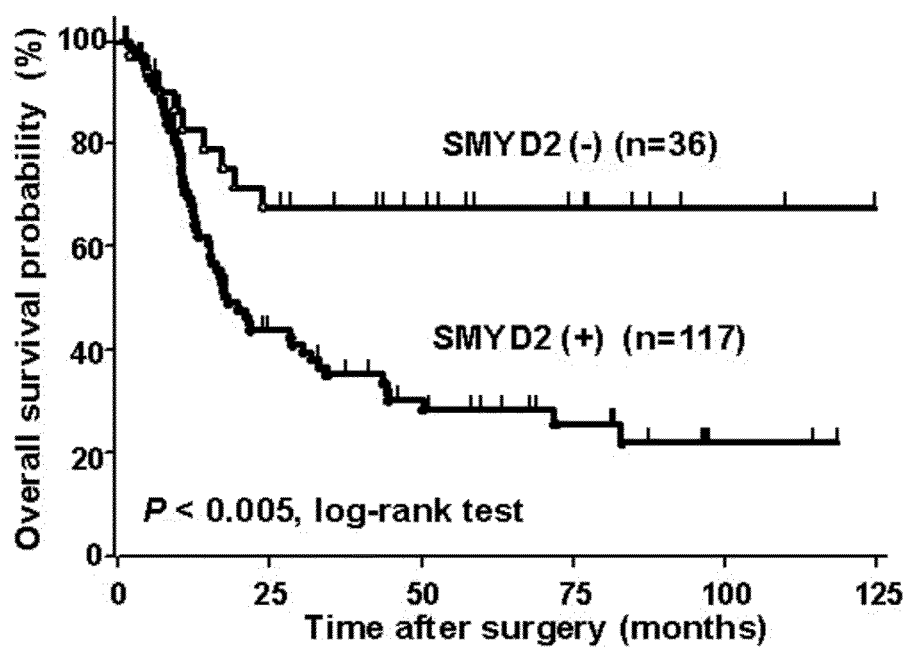

Confirmation of High-Level Expression of SMYD2 Protein in Esophageal Squamous Cell Carcinoma and Correlation Between Such Expression and Prognosis For examination of the expression conditions of SMYD2 in ESCC, 153 primary esophageal carcinoma specimens were subjected to immunohistochemical staining (upper column of FIG. 10). Also, the relationship between days elapsed after treatment and survival rates is shown with a survival curve (lower column of FIG. 10).

Immunohistochemical staining was carried out by an ABC method. Specifically, the method is carried out by formalin fixation of paraffin embedded tissue sections. Each section on a silane-coated glass slide was subjected to deparaffinization and stepwise dehydration using ethanol. An antigen was subjected to warm bath treatment at 95° C. for 40 minutes in 10 mM Citrate Buffer (pH 6.0). Endogenous peroxidase was inhibited using 5% hydrogen peroxide. Next, Avidin, Biotin Block treatment was carried out according to protocols using an Avidin Biotin Blocking Kit (VECTOR, Cat No. SP-2001). Next, an SMYD2 antibody as a primary antibody was diluted 200-fold, followed by overnight reaction at 4° C. The resultant was washed in the next morning and then reacted for 1 hour with a biotin-labeled secondary antibody diluted 100-fold. After washing, a mixed solution of Avidin diluted 100-fold and Biotin diluted 100-fold was applied to each sample according to protocols using an ABC Kit (VECTOR, Cat No. PK-4000), followed by approximately 1 hour of reaction. After washing, the resultant was blended well with TBS (Tris-Buffered Saline pH 7.6+0.3% tween 20) and then color development was caused using DAB. Counter staining was then carried out using mayer hematoxylin. The resultant was washed in running water, dehydrated with an ascending series of ethanol, and then cleared with xylol.

The immunostaining pattern of SMYD2 is shown in the upper column of FIG. 10. Normal esophageal mucosa was not stained, but particularly positive findings were observed at parts invaded by tumors. 117 out of 153 specimens were positive for immunostaining. Also, as shown in the lower column of FIG. 10, it was revealed that cases with high-level expression of the SMYD2 protein showed extremely poor prognoses (p<0.005).

Example 12

Association with Clinicopathologic Characteristics

Examination via comparison of the above 153 primary esophageal carcinoma specimens with clinicopathologic characteristics was carried out. As a result, cases expressing the SMYD2 protein at high levels were found to be significantly positive for venous invasion, show deep tumor invasion depths, and show high recurrence frequencies (Table 3). Multivariate analysis using the Cox proportional hazards model revealed that SMYD2 is an independent prognostic factor (Table 4).

TABLE 3

The presence or the absence of SMYD2 expression in 153 clinical specimens of esophageal squamous cell carcinoma and correlation of the same with clinicopathologic characteristics Association between clinicopathologic characteristics and SMYD2 expression

| | | SMYD2 immunoreactivity | | |
|---|---|---|---|---|
| | n | Positive (%) | Negative (%) | P value* |
| Total | 153 | 117 (76.5) | 36 (23.5) | |
| Gender | | | | |
| Male | 128 | 102 (79.7) | 26 (20.3) | 0.0338 |
| Female | 25 | 15 (60.0) | 10 (40.0) | |
| Age (y) | | | | |
| Mean | 63.7 | | | |
| ≥60 | 102 | 76 (74.5) | 26 (25.5) | 0.4187 |
| <60 | 51 | 41 (80.4) | 10 (19.6) | |
| Location† | | | | |
| Upper | 25 | 21 (84.0) | 4 (16.0) | 0.2366 |
| Middle | 79 | 56 (70.9) | 23 (29.1) | |
| Lower | 49 | 40 (81.6) | 9 (18.4) | |
| Histopathological Grading | | | | |
| Well - moderately differentiated | 137 | 107 (78.1) | 30 (21.9) | 0.2797 |
| poorly differentiated | 16 | 10 (62.5) | 6 (37.5) | |
| Venous invasion | | | | |
| 0 | 40 | 24 (60.0) | 16 (40.0) | 0.0042 |
| 1-3 | 113 | 93 (82.3) | 20 (17.7) | |
| Lymphatic invasion | | | | |
| 0 | 18 | 11 (61.1) | 7 (38.9) | 0.1803 |
| 1-3 | 135 | 106 (78.5) | 29 (21.5) | |
| TNM classification | | | | |
| pT categories | | | | |
| pT1 | 17 | 11 (64.7) | 6 (35.3) | 0.0208 |
| pT2/3 | 97 | 70 (72.2) | 27 (27.8) | |
| pT4 | 39 | 36 (92.3) | 3 (7.7) | |
| pN categories | | | | |
| 0 | 34 | 26 (76.5) | 8 (23.5) | 0.8186 |
| 1 | 119 | 91 (76.5) | 28 (23.5) | |

TABLE 3-continued

The presence or the absence of SMYD2 expression in 153 clinical specimens of esophageal squamous cell carcinoma and correlation of the same with clinicopathologic characteristics Association between clinicopathologic characteristics and SMYD2 expression

| | | SMYD2 immunoreactivity | | |
|---|---|---|---|---|
| | n | Positive (%) | Negative (%) | P value* |
| pM categories | | | | |
| 0 | 126 | 97 (77.0) | 29 (23.0) | 0.9413 |
| 1 | 27 | 20 (74.1) | 7 (25.9) | |
| pStage | | | | |
| I | 7 | 4 (57.1) | 3 (42.9) | 0.6702 |
| II | 37 | 29 (78.4) | 8 (21.6) | |
| III | 78 | 60 (76.9) | 18 (23.1) | |
| IV | 31 | 24 (77.4) | 7 (22.6) | |
| Recurrennce | | | | |
| Absent | 77 | 51 (66.2) | 26 (33.8) | 0.0049 |
| Precent | 76 | 66 (86.8) | 10 (13.2) | |
| p53 immunoreactivity | | | | |
| Negative | 79 | 64 (81.0) | 15 (19.0) | 0.7013 |
| Positive | 74 | 53 (71.6) | 21 (28.4) | |

NOTE.
Statiststically significant values are in boldface type.
*P values are from ?² or Fisher's exact test and were statistically significant when <0.05.
†Upper, cervical + upper thoracic esophagus; Middle, mid-thoracic esophagus; Lower, lower thoracic + abdominal esophagus.

TABLE 4

Univariate analysis and multivariate analysis regarding prognostic factor in 153 clinical specimens of esophageal squamous cell carcinoma Cox proportional hazard regression analysis for overall survival

| | Univariate | | | |
|---|---|---|---|---|
| Factor | Hazard ratio (95% confidence interval) | P-value* | Multivariate⁺ P-value* |
| Gender | | | |
| Male versus | 2.033 (1.006-4.115) | 0.0481 | 0.0265 |
| Age (y) | | | |
| >60 versus <60 | 0.805 (0.497-1.302) | 0.376 | X |
| Histopathological | | | |
| poor versus well-moderate | 1.123 (0.537-2.351) | 0.7575 | X |
| Venous invasion | | | |
| 1-3 versus 0 | 2.445 (1.368-4.367) | 0.0025 | X |
| Lymphatic invasion | | | |
| 1-3 versus 0 | 2.786 (1.116-6.944) | 0.0282 | X |
| TNM classification pT categories | | | |
| pT2-4 versus pT1 | 4.505 (1.410-14.286) | 0.011 | X |
| pN categories | | | |
| pN1 versus pN0 | 3.236 (1.546-6.803) | 0.0019 | X |
| pM categories⁺ | | | |
| pM1 versus pM0 | 1.898 (1.049-3.425) | 0.034 | X |
| pStage | | | |
| III + IVversus | 3.012 (1.667-5.435) | 0.0003 | <0.0001 |
| SMYD2 expression¤ | | | |
| positive versus negative | 2.849 (1.410-5.780) | 0.0035 | 0.0025 |
| p53 | | | |
| positive versus negative | 0.923 (0.572-1.490) | 0.7438 | X |

NOTE.
Statiststically significant values are in boldface
*p-values are from two-sided tests and were statistically significant when <0.05.
⁺Forward- and backward-stepwise analyses were used for multivariate analysis.
⁻All of the M1 tumors had distant lymph node metastases but no organ
¤SMYD2 expression was evaluated by immunohistochemical analysis as described in Materials and Methods.

Example 13

Figure 11:
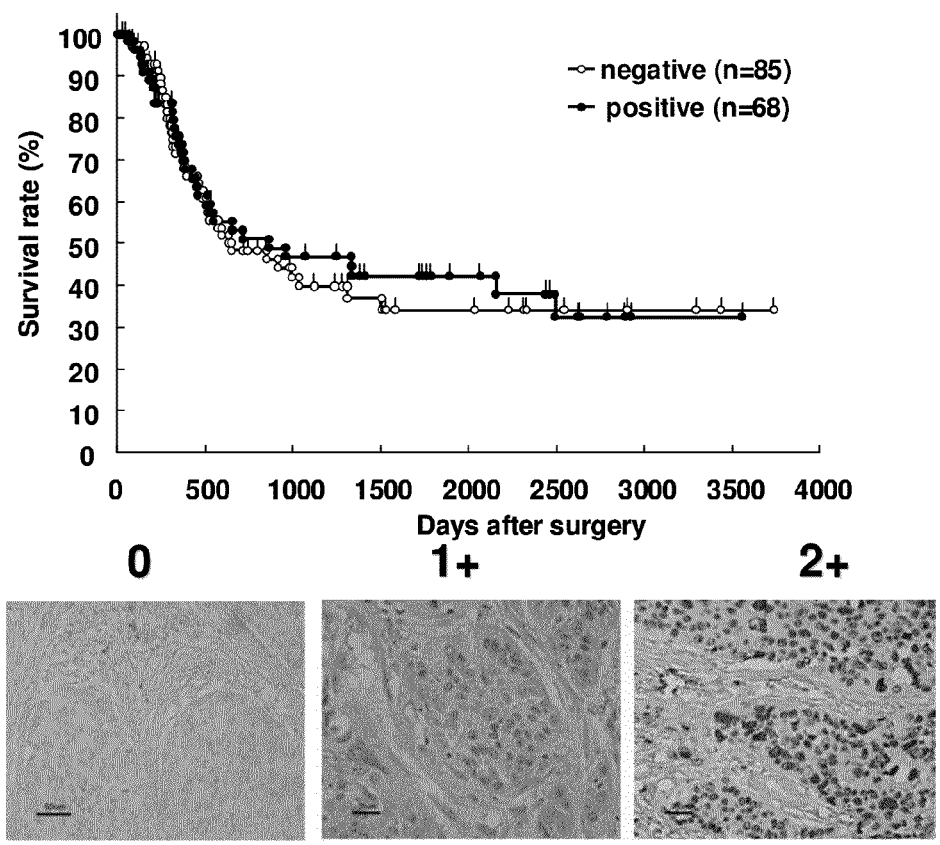
FIG. 11 shows the results of analyzing the expression levels of the p53 protein by an immunohistochemical staining method. In the graph in the upper column, the horizontal axis indicates days elapsed after treatment and the longitudinal axis indicates survival rates. The lower column indicates the staining conditions of p53 as revealed by the immunohistochemical staining method.

Analysis of Correlation Between p53 Expression Pattern and Prognosis and Analysis of Correlation Between p53 Expression and SMYD2 Expression The results of analyzing the p53 expression pattern and prognosis are shown in the upper column of FIG. 11. Also, the results of analyzing the expression levels of the p53 protein by an immunohistochemical staining method are shown in the lower column of FIG. 11.

Cases found to be positive or negative by immunohistochemical staining of the p53 protein showed no difference in prognosis (FIG. 11). Also, no correlation was confirmed between p53 expression and SMYD2 expression.

Example 14

Correlation Between the Presence or the Absence of SMYD2/p53 Protein Expression and Prognosis Correlation between the presence or the absence of SMYD2 and p53 protein expression and prognosis was analyzed by immunohistological staining.

Figure 12:
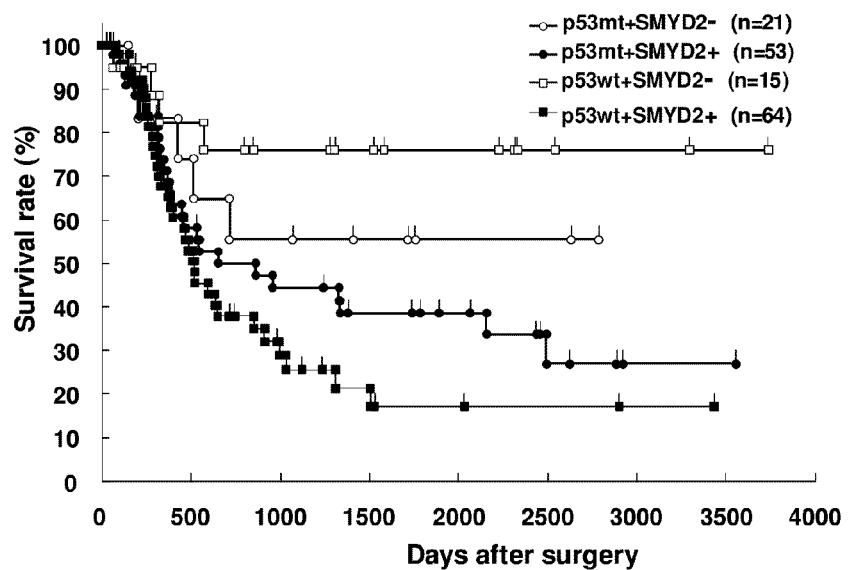
FIG. 12 shows the relationship between SMYD2 and p53protein expression and the survival rates in 153 ESCC cases.

FIG. 12 shows the results. p53-negative (normal p53) and SMYD2-positive cases were found to show the poorest prognosis. Conversely, p53-negative (normal p53) and SMYD2-expression-negative cases were found to show extremely good prognosis. In addition, it was revealed that SMYD2 is a prognostic factor independent from p53 expression (FIG. 12).

FIG. 13 shows evaluation of the accuracy of the prepared SNYD2 specific antibody. HLE (human hepatoma cell line), KYSE200, and KYSE510 cell lines were used as negative controls, and the KYSE150 cell line was used as a positive control. Moreover, evaluation was also carried out using a pCMV-3tag4A-SMYD2 overexpression systems for KYSE200 and KYSE510.

FIG. 14 shows confirmation of induction of p21 expression by SMYD2 knockdown for an SaOS2 (p53 null cell line) cell line. Hence, it was suggested that SMYD2 may be involved in cell growth independently of p53.

CONCLUSION

The results of Examples 1 to 14 are as summarized as follows.

(1) It was discovered by screening using an array CGH method that the 1q32-1q41 gene region is a new cancer marker for esophageal carcinoma.

(2) It was discovered that the SMYD2 gene contained in the 1q32-1q41 chromosomal region is a more preferable cancer marker.

(3) It was revealed that SMYD2 gene expression accelerates the cell growth of esophageal carcinoma.

The invention claimed is:

1. A method for treating esophageal carcinoma in a subject, which comprises:
   detecting the amount of each of SMYD2 protein and p53 protein in a specimen from esophagus;
   detecting positive expression of SMYD2 and negative expression of p53;
   determining poor prognosis in a subject when p53 expression is negative and SMYD2 expression is positive; and
   administering to the poor prognosis subject an siRNA of an SMYD2 gene as set forth in SEQ ID NO: 3 or an antisense oligonucleotide of an SMYD2 gene (SEQ ID NO: 1).

2. The method according to claim 1, wherein the amount of each of SMYD2 protein and p53 protein is detected by an immunohistochemical method.

3. The method according to claim 1, wherein canceration including malignancy within the specimen, is detected.

* * * * *